(12) United States Patent
He et al.

(10) Patent No.: US 7,398,013 B2
(45) Date of Patent: Jul. 8, 2008

(54) VAPORIZER FEATURES

(75) Inventors: Mengtao Pete He, Scottsdale, AZ (US); Carl Triplett, Scottsdale, AZ (US); Mary J. Conway, Phoenix, AZ (US)

(73) Assignee: The Dial Corporation, Scottsdale, AZ (US)

( * ) Notice: Subject to any disclaimer, the term of this patent is extended or adjusted under 35 U.S.C. 154(b) by 849 days.

(21) Appl. No.: 10/650,173

(22) Filed: Aug. 28, 2003

(65) Prior Publication Data

US 2004/0247300 A1    Dec. 9, 2004

Related U.S. Application Data

(60) Provisional application No. 60/407,393, filed on Aug. 30, 2002, provisional application No. 60/407,387, filed on Aug. 30, 2002.

(51) Int. Cl.
*F24F 6/00* (2006.01)
(52) U.S. Cl. ..................... 392/394; 392/390
(58) Field of Classification Search ......... 392/386–406; 239/34–56, 135, 136
See application file for complete search history.

(56) References Cited

U.S. PATENT DOCUMENTS

| | | | |
|---|---|---|---|
| 1,836,600 A | 12/1931 | Jones | |
| 3,262,290 A | 7/1966 | Huber | |
| 3,748,438 A | 7/1973 | Costello | |
| 3,780,260 A | 12/1973 | Eisner | |
| 3,895,928 A | 7/1975 | Gonzalo | |
| 3,908,905 A | 9/1975 | Von Philipp et al. | |
| 3,923,458 A | 12/1975 | Gonzalo | |
| 3,948,445 A | 4/1976 | Andweg | |
| 4,017,030 A | 4/1977 | Coplan et al. | |
| 4,037,353 A | 7/1977 | Hennart et al. | |
| 4,084,079 A | 4/1978 | Costello | |
| 4,111,655 A | 9/1978 | Quincey | |
| 4,123,741 A | 10/1978 | Kiyono et al. | |
| 4,165,835 A | 8/1979 | Dearling | |
| 4,171,340 A | 10/1979 | Nishimura et al. | |
| 4,208,012 A | 6/1980 | Dutcher | |
| 4,214,146 A | 7/1980 | Schimanski | |
| 4,220,281 A | 9/1980 | Martens, III et al. | |
| 4,228,124 A | 10/1980 | Kashihara et al. | |

(Continued)

FOREIGN PATENT DOCUMENTS

DE    35 35 564    5/1986

(Continued)

OTHER PUBLICATIONS

PCT International Preliminary Examination Report issued Aug. 10, 2004 for International Application No. PCT/US03/26754, International Filing Date Aug. 28, 2003, 4 pages.

(Continued)

*Primary Examiner*—Sang Paik
(74) *Attorney, Agent, or Firm*—Snell & Wilmer LLP

(57) ABSTRACT

The present invention provides vapor dispensing devices having improved refill units, detectors which sense changes in the environments surrounding the device, and optionally, make corresponding changes to the device and/or auxiliary devices, volatizable material delivery systems, volatizable material enhancers and various other features.

12 Claims, 16 Drawing Sheets

U.S. PATENT DOCUMENTS

| | | | |
|---|---|---|---|
| 4,243,969 A | 1/1981 | Steigerwald et al. |
| 4,293,173 A | 10/1981 | Tricca |
| 4,294,778 A | 10/1981 | DeLuca |
| 4,346,059 A | 8/1982 | Spector |
| 4,391,781 A | 7/1983 | Van Lit |
| 4,408,813 A | 10/1983 | Koehler |
| 4,413,779 A | 11/1983 | Santini |
| 4,415,797 A | 11/1983 | Choustoulakis |
| 4,425,302 A | 1/1984 | Pons Pons |
| 4,467,177 A | 8/1984 | Zobele |
| 4,518,212 A | 5/1985 | Rumble |
| 4,530,556 A | 7/1985 | Bonus |
| 4,537,351 A | 8/1985 | Wilson |
| 4,544,592 A | 10/1985 | Spector |
| 4,549,250 A | 10/1985 | Spector |
| 4,556,539 A | 12/1985 | Spector |
| 4,571,485 A | 2/1986 | Spector |
| 4,574,181 A | 3/1986 | Spector |
| 4,595,564 A | 6/1986 | Spector et al. |
| 4,631,387 A | 12/1986 | Glucksman |
| 4,658,985 A | 4/1987 | Madsen et al. |
| 4,660,764 A | 4/1987 | Joyaux et al. |
| 4,662,679 A | 5/1987 | Franck |
| 4,675,504 A | 6/1987 | Suhajda |
| 4,686,353 A | 8/1987 | Spector |
| 4,695,434 A | 9/1987 | Spector |
| 4,703,155 A | 10/1987 | Suhajda |
| 4,707,336 A | 11/1987 | Jones |
| 4,714,984 A | 12/1987 | Spector |
| 4,718,856 A | 1/1988 | Pinkerton et al. |
| 4,725,712 A | 2/1988 | Schroeder |
| 4,731,520 A | 3/1988 | Glucksman |
| 4,731,522 A | 3/1988 | Manchester |
| 4,732,321 A | 3/1988 | Dolan |
| 4,734,560 A | 3/1988 | Bowen |
| 4,739,928 A | 4/1988 | O'Neil |
| 4,743,406 A | 5/1988 | Steiner et al. |
| 4,753,389 A | 6/1988 | Davis |
| 4,777,345 A | 10/1988 | Manchester |
| 4,780,286 A | 10/1988 | Parent et al. |
| 4,795,883 A | 1/1989 | Glucksman et al. |
| 4,798,935 A | 1/1989 | Pezaris |
| 4,800,239 A | 1/1989 | Hill |
| 4,801,271 A | 1/1989 | Piper |
| 4,804,821 A | 2/1989 | Glucksman |
| 4,808,347 A | 2/1989 | Dawn |
| 4,816,973 A | 3/1989 | Atalla et al. |
| 4,830,791 A | 5/1989 | Muderlak et al. |
| 4,837,421 A | 6/1989 | Luthy |
| 4,849,606 A | 7/1989 | Martens, III et al. |
| 4,853,517 A | 8/1989 | Bowen et al. |
| 4,878,615 A | 11/1989 | Losi |
| 4,886,469 A | 12/1989 | Jseng |
| 4,915,301 A | 4/1990 | Munteanu |
| 4,919,981 A | 4/1990 | Levey et al. |
| 4,931,224 A | 6/1990 | Holzner, Sr. |
| 4,931,258 A | 6/1990 | Zlotnik et al. |
| 4,968,456 A | 11/1990 | Muderlak et al. |
| D315,789 S | 3/1991 | Muderlak |
| 4,998,671 A | 3/1991 | Leifheit |
| 5,004,435 A | 4/1991 | Jammet |
| 5,014,913 A | 5/1991 | Hoyt et al. |
| 5,015,442 A | 5/1991 | Hirai |
| 5,029,729 A | 7/1991 | Madsen et al. |
| 5,038,394 A | 8/1991 | Hasegawa et al. |
| 5,050,798 A | 9/1991 | Sullivan |
| 5,106,317 A | 4/1992 | Taylor |
| 5,111,477 A | 5/1992 | Muderlak |
| 5,115,975 A | 5/1992 | Shilling |
| 5,121,881 A | 6/1992 | Lembeck |
| 5,126,078 A | 6/1992 | Steiner et al. |
| 5,136,684 A | 8/1992 | Lonker et al. |
| 5,147,582 A | 9/1992 | Holzner, Sr. et al. |
| 5,148,984 A | 9/1992 | Bryson, Jr. et al. |
| 5,175,791 A | 12/1992 | Muderlak et al. |
| 5,196,171 A | 3/1993 | Peltier |
| 5,201,025 A | 4/1993 | Landesberg |
| 5,217,696 A | 6/1993 | Wolverton et al. |
| 5,220,636 A | 6/1993 | Chang |
| 5,222,186 A | 6/1993 | Schimanski et al. |
| 5,223,182 A | 6/1993 | Steiner et al. |
| 5,233,680 A | 8/1993 | Fussell |
| 5,239,610 A | 8/1993 | Shao |
| 5,240,426 A | 8/1993 | Barla |
| 5,285,014 A | 2/1994 | Gilchrist |
| 5,290,546 A | 3/1994 | Hasegawa et al. |
| 5,295,845 A | 3/1994 | Changxing |
| 5,314,669 A | 5/1994 | Hamilton |
| 5,320,542 A | 6/1994 | Cheng |
| 5,339,065 A | 8/1994 | Slenker |
| 5,342,584 A | 8/1994 | Fritz et al. |
| 5,373,581 A | 12/1994 | Smith |
| 5,375,728 A | 12/1994 | West |
| 5,376,338 A | 12/1994 | Zlotnik |
| 5,382,410 A | 1/1995 | Peltier |
| D355,251 S | 2/1995 | Paulovich et al. |
| 5,394,506 A | 2/1995 | Stein et al. |
| 5,402,517 A | 3/1995 | Gillett et al. |
| D357,330 S | 4/1995 | Wong et al. |
| 5,431,859 A | 7/1995 | Tobin |
| 5,431,885 A | 7/1995 | Zlotnik et al. |
| 5,445,802 A | 8/1995 | Wendelken |
| 5,465,198 A | 11/1995 | Kellogg |
| 5,480,591 A | 1/1996 | Lagneaux et al. |
| 5,481,442 A | 1/1996 | Wiltshire et al. |
| 5,484,086 A | 1/1996 | Pu |
| 5,498,397 A | 3/1996 | Horng |
| 5,521,357 A | 5/1996 | Lock et al. |
| 5,522,008 A | 5/1996 | Bernard |
| 5,547,616 A | 8/1996 | Dancs et al. |
| 5,556,192 A | 9/1996 | Wang |
| 5,567,361 A | 10/1996 | Harper |
| 5,574,821 A | 11/1996 | Babasade |
| 5,575,992 A | 11/1996 | Kunze |
| 5,577,156 A | 11/1996 | Costello |
| 5,591,395 A | 1/1997 | Schroeder et al. |
| 5,624,230 A | 4/1997 | Taylor et al. |
| 5,634,806 A | 6/1997 | Hahn |
| 5,647,052 A | 7/1997 | Patel et al. |
| 5,647,053 A | 7/1997 | Schroeder et al. |
| 5,651,942 A | 7/1997 | Christinsen |
| 5,662,835 A | 9/1997 | Collingwood |
| 5,664,958 A | 9/1997 | Chadwick et al. |
| 5,700,430 A | 12/1997 | Bonnema et al. |
| 5,735,460 A | 4/1998 | Eisenbraun |
| 5,749,520 A | 5/1998 | Martin et al. |
| 5,750,498 A | 5/1998 | Soeda et al. |
| 5,765,751 A | 6/1998 | Joshi |
| 5,788,155 A | 8/1998 | Martin et al. |
| 5,788,931 A | 8/1998 | Munoz Quintana |
| 5,796,914 A | 8/1998 | Gatzemeyer et al. |
| 5,805,768 A | 9/1998 | Schwartz et al. |
| 5,810,265 A | 9/1998 | Cornelius et al. |
| 5,813,873 A | 9/1998 | McBain et al. |
| 5,832,648 A | 11/1998 | Malone |
| 5,873,529 A | 2/1999 | Johnson |
| 5,875,968 A | 3/1999 | Miller et al. |
| 5,884,808 A | 3/1999 | Muderlak et al. |
| 5,899,381 A | 5/1999 | Gordon et al. |
| 5,903,710 A | 5/1999 | Wefler et al. |
| 5,926,614 A | 7/1999 | Steinel |
| 5,928,605 A | 7/1999 | Bonnema et al. |
| 5,932,204 A | 8/1999 | Joshi |
| 5,937,140 A | 8/1999 | Leonard et al. |

| | | |
|---|---|---|
| 5,940,577 A | 8/1999 | Steinel |
| 5,944,223 A | 8/1999 | Klima et al. |
| 5,945,094 A | 8/1999 | Martin et al. |
| 5,955,701 A | 9/1999 | Schockner et al. |
| 5,957,701 A | 9/1999 | McMillin |
| 5,970,643 A | 10/1999 | Gawel, Jr. |
| 5,976,503 A | 11/1999 | Martin et al. |
| 5,998,735 A | 12/1999 | Patterson, Jr. |
| 6,021,254 A | 2/2000 | Hunter |
| 6,031,967 A | 2/2000 | Flashinski et al. |
| 6,032,930 A | 3/2000 | Calino |
| 6,036,536 A | 3/2000 | Chiu |
| 6,044,202 A | 3/2000 | Junkel |
| 6,045,374 A | 4/2000 | Candeloro |
| 6,050,551 A | 4/2000 | Anderson |
| 6,051,788 A | 4/2000 | Nichols |
| 6,078,728 A | 6/2000 | O'Rourke et al. |
| 6,085,026 A | 7/2000 | Hammons et al. |
| 6,097,881 A | 8/2000 | DeWitt et al. |
| 6,099,137 A | 8/2000 | McCormick et al. |
| 6,101,315 A | 8/2000 | Steinel, Jr. |
| 6,104,866 A | 8/2000 | DeWitt et al. |
| 6,104,867 A | 8/2000 | Stathakis et al. |
| D430,659 S | 9/2000 | Zaraboza et al. |
| 6,123,935 A | 9/2000 | Wefler et al. |
| 6,141,496 A | 10/2000 | Sundberg et al. |
| 6,148,143 A | 11/2000 | Steinel, Jr. |
| 6,156,088 A | 12/2000 | Cardarelli |
| 6,197,262 B1 | 3/2001 | Del Ben |
| 6,197,263 B1 | 3/2001 | Blount |
| 6,227,118 B1 | 5/2001 | Nance |
| 6,236,807 B1 | 5/2001 | Ruffolo et al. |
| 6,249,645 B1 | 6/2001 | Smith |
| 6,254,065 B1 | 7/2001 | Ehrensperger et al. |
| 6,264,548 B1 | 7/2001 | Payne, Jr. et al. |
| 6,269,979 B1 | 8/2001 | Dumont |
| 6,270,720 B1 | 8/2001 | Mandish |
| 6,275,651 B1 | 8/2001 | Voit |
| 6,278,840 B1 | 8/2001 | Basaganas Millan |
| 6,285,830 B1 | 9/2001 | Basaganas Millan |
| 6,289,176 B1 | 9/2001 | Martter et al. |
| 6,302,559 B1 | 10/2001 | Warren |
| 6,315,959 B2 | 11/2001 | Mandish |
| 6,328,791 B1 | 12/2001 | Pillion et al. |
| 6,342,676 B1 | 1/2002 | Ha |
| 6,349,168 B1 | 2/2002 | Jaworski |
| 6,352,210 B1 | 3/2002 | Requejo |
| 6,354,513 B1 | 3/2002 | Basaganas Millan |
| 6,361,752 B1 | 3/2002 | Demarest et al. |
| 6,364,673 B1 | 4/2002 | Lee |
| 6,368,564 B1 | 4/2002 | Smith |
| 6,371,815 B1 | 4/2002 | Wetzel et al. |
| 6,374,044 B1 | 4/2002 | Freidel |
| 6,374,045 B2 | 4/2002 | Basaganas Millan |
| 6,381,408 B1 | 4/2002 | Jaworski et al. |
| 6,603,924 B2 | 8/2003 | Brown et al. |
| 6,667,006 B2 * | 12/2003 | Richards ........................ 422/4 |
| 6,714,725 B2 | 3/2004 | Grone et al. |
| 6,766,817 B2 | 7/2004 | da Silva |
| 6,853,801 B2 * | 2/2005 | Wefler ........................ 392/392 |
| 2001/0031225 A1 | 10/2001 | Mandish |
| 2001/0053283 A1 | 12/2001 | Levine et al. |
| 2002/0144992 A1 | 10/2002 | Vieira |
| 2003/0138241 A1 | 7/2003 | Ambrosi et al. |

FOREIGN PATENT DOCUMENTS

| | | |
|---|---|---|
| DE | 41 31 613 | 3/1993 |
| EP | 0 296 807 | 12/1988 |
| EP | 0 669 137 | 8/1995 |
| EP | 0 911 041 | 4/1999 |
| GB | 402507 | 12/1933 |
| GB | 2 356 815 | 6/2001 |
| WO | WO 00 76292 | 12/2000 |
| WO | WO 01 10739 | 2/2001 |
| WO | WO 01/68154 | 9/2001 |
| WO | WO 01/93919 | 12/2001 |

OTHER PUBLICATIONS

PCT International Search Report issued Dec. 17, 2003 for International Application No. PCT/US03/26511, International Filing Date Aug. 26, 2003, 4 pages.
PCT International Search Report issued Apr. 21, 2004 for International Application No. PCT/US03/26754, International Filing Date Aug. 28, 2003, 4 pages.
PCT International Search Report issued Nov. 12, 2003 for International Application No. PCT/US03/25245, International Filing Date Aug. 31, 2003, 4 pages.
PCT International Search Report issued Oct. 7, 2003 for International Application No. PCT/US03/04082, International Filing Date Feb. 12, 2003, 8 pages.
PCT International Search Report issued Dec. 16, 2003 for International Application No. PCT/US03/25244, International Filing Date Aug. 13, 2003, 3 pages.
PCT International Search Report issued Dec. 16, 2003 for International Application No. PCT/US03/25246, International Filing Date Aug. 13, 2003, 3 pages.
PCT International Search Report issued Dec. 19, 2003 for International Application No. PCT/US03/25243, International Filing Date Aug. 13, 2003, 4 pages.
Brochure-"Decora Devices," by Leviton, date unknown, Section A, pp. A1-A36.

* cited by examiner

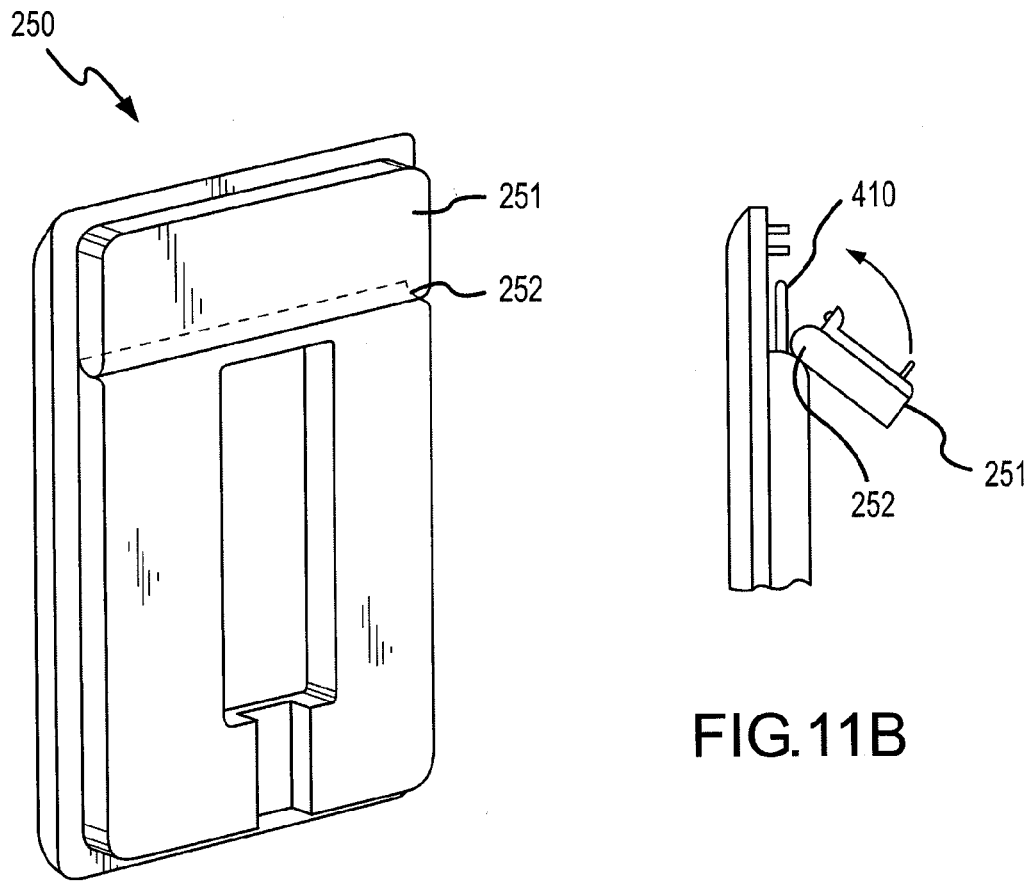
FIG.11B
FIG.11A
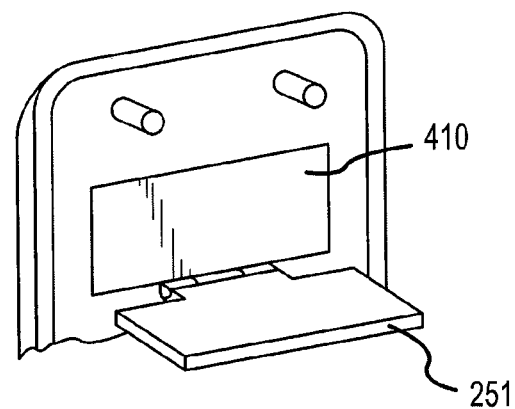
FIG.11C

VAPORIZER FEATURES

CROSS-REFERENCE TO RELATED APPLICATIONS

This application claims priority to U.S. Provisional Patent Application Ser. No. 60/407,393 entitled "Vaporizer Features," filed Aug. 30, 2002 and to U.S. Provisional Patent Application Ser. No. 60/407,387 entitled "Wall-Mounted Electrical Device Having Adjustable Outlet Prongs," filed Aug. 30, 2002 which are incorporated herein by reference.

TECHNICAL FIELD

This invention relates, generally, to vapor dispensing devices and various features of the same.

BACKGROUND INFORMATION

Vapor-dispensing products typically include a volatizable material and a transport system configured to facilitate evaporation of the volatizable material into the surrounding air. For example, in some systems, a liquid is contained in a reservoir bottle; in others, a wax or gel-type material is used. The housing, which typically protrudes from a wall outlet, facilitates the evaporation of the volatizable material into the environment. In such devices, a heating element may deliver kinetic energy to molecules of the volatizable material. Such units are plugged into a conventional electrical outlet, thereby causing the heating element to heat the liquid (or wax) and cause evaporation.

Known vapor-dispensing devices of this type may be improved in a number of respects. For example, various vapor-dispensing devices (e.g., room freshener's and the like) that interface with wall outlets may benefit from improved stability and/or improved access to and use of one or more of the wall outlets. It may also be desirable that refill units for the device have improved features relating to stability and its "state" (e.g., the amount of material left in the refill). Improved fragrance delivery systems are likewise desirable. Additionally, it is often desirable to have improved dispensation of the material to be vaporized as well as having the ability to increase delivery of the material at various times. Still other benefits may be realized from improved indicators of the status of the dispensing units. Further still, benefits may be realized from the ability for the outlet prongs to adjust to various shaped outlet receptacles.

Thus, there is a need for a vapor-dispensing device that overcomes these and other limitations of the prior art.

SUMMARY OF THE INVENTION

While the way in which the present invention addresses the disadvantages of the prior art will be discussed in greater detail below, in general, the present invention provides vapor dispensing devices having improved refill units, detectors which sense changes in the environments surrounding the device, and optionally, make corresponding changes to the device and/or auxiliary devices, volatizable material delivery systems, volatizable material enhancers and various other features.

BRIEF DESCRIPTION OF THE DRAWINGS

The subject invention will hereinafter be described in conjunction with the appended drawing figures, wherein like numerals denote like elements.

FIGS. 11A-C are views of an alternative refill in accordance with various aspects of the present invention;

DETAILED DESCRIPTION

The following description is of exemplary embodiments of the invention only, and is not intended to limit the scope, applicability or configuration of the invention in any way. Rather, the following description is intended to provide a convenient illustration for implementing various embodiments of the invention. As will become apparent, various changes may be made in the function and arrangement of the elements described in these embodiments without departing from the scope of the invention as set forth herein. For example, in the context of the present invention, the method and apparatus hereof find particular use in connection with air freshening vaporizer systems. However, generally speaking, various volatizable materials such as insect repellants, deodorizers, sanitizers, and/or the like are suitable for use in accordance with the present invention.

Similarly, for illustrative purposes, the present invention is oft-described with reference to a multiple-outlet vapor-dispensing device (e.g., a dual-outlet air-freshener) configured to interface, for example, with standard dual-outlet, quad-outlet, or such other electrical receptacles, to substantially maintain (or, indeed, augment) the functionality of the electrical receptacle with which the vapor-dispensing device interfaces. However, it should be appreciated that the description herein may likewise be adapted to be employed with alternatively configured devices having different shapes, components, plugs, and the like and still fall within the scope of the present invention.

Figure 1:
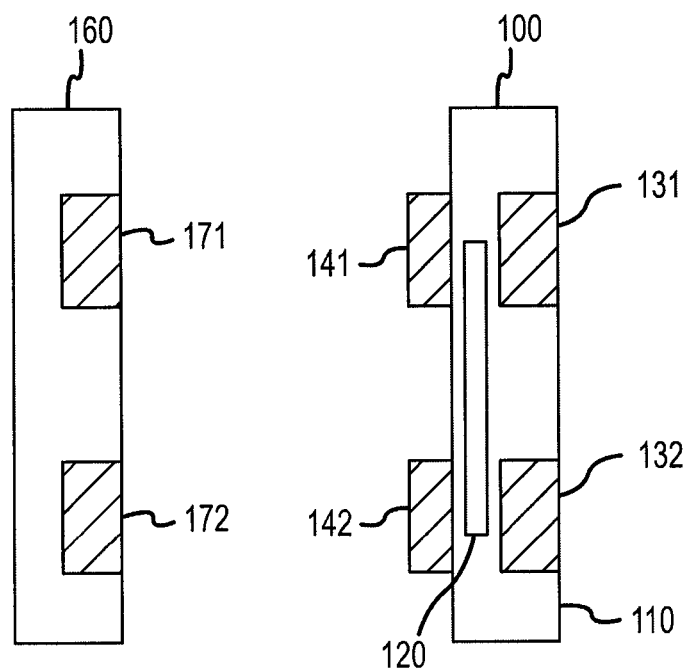
FIG. 1 is an exemplary vapor-dispensing device in accordance with an exemplary embodiment of the present invention.
Figure 2:
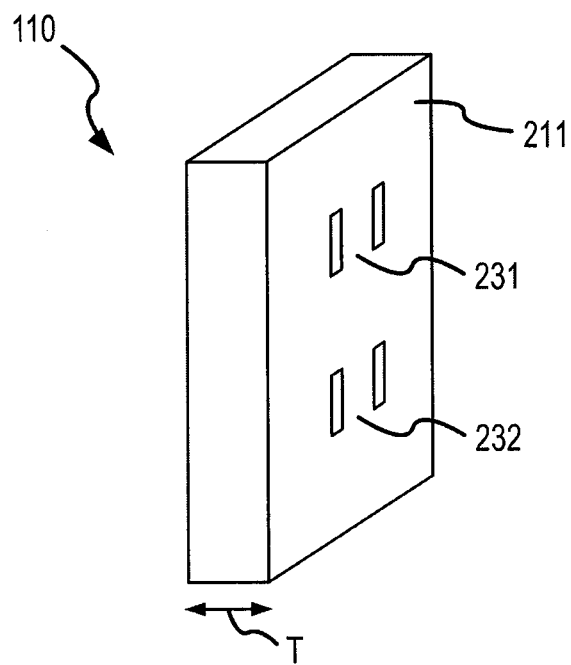
FIGS. 2 and 3 are perspective views of housings in accordance with exemplary embodiments of the present invention.
Figure 3:
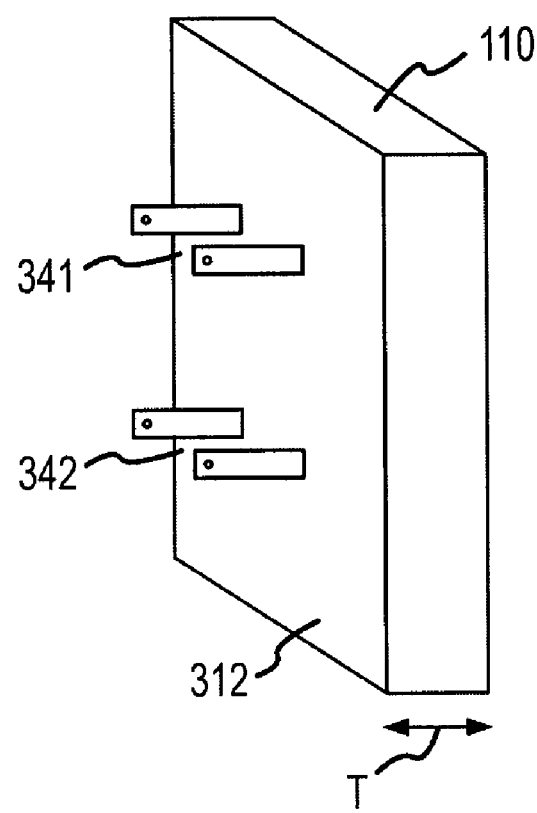

That being said, FIG. 1 illustrates, an exemplary vapor-dispensing device 100 configured to attach to an electrical receptacle 160. In general, vapor-dispensing device 100 suitably comprises a housing 110, at least one plug 141, two device outlets 131 and 132, and a fragrance delivery system 120.

With reference to FIGS. 1-4, and in accordance with various exemplary embodiments of the present invention, housing 110 comprises a front surface 211 and a back surface 312 separated by a thickness T. The front 211 and back 312 surfaces may generally conform to the geometry of the mating electrical receptacle 160 (and/or a face-plate associated with electrical receptacle 160), or may have any convenient shape. For example, a rectangular housing 110 may be configured to be approximately the same size as a standard rectangular wall plate for a duplex electrical receptacle (e.g., 160). The use of approximately similar dimensions for the height and width of housing 110 as on electrical receptacle 160, and the use of a narrow thickness T, aids in reducing the visibility (or increasing the "discreteness") of vapor-dispensing device 100. In accordance with this illustrative embodiment of the present invention, vapor-dispensing device 100 is configured such that, when connected to electrical receptacle 160, vapor-dispensing device 100 generally mimics a standard wall outlet plate so as to make the device less noticeable to those in the vicinity of the device and to allow functional access to one or more outlets of electrical receptacle 160.

Figure 4A:
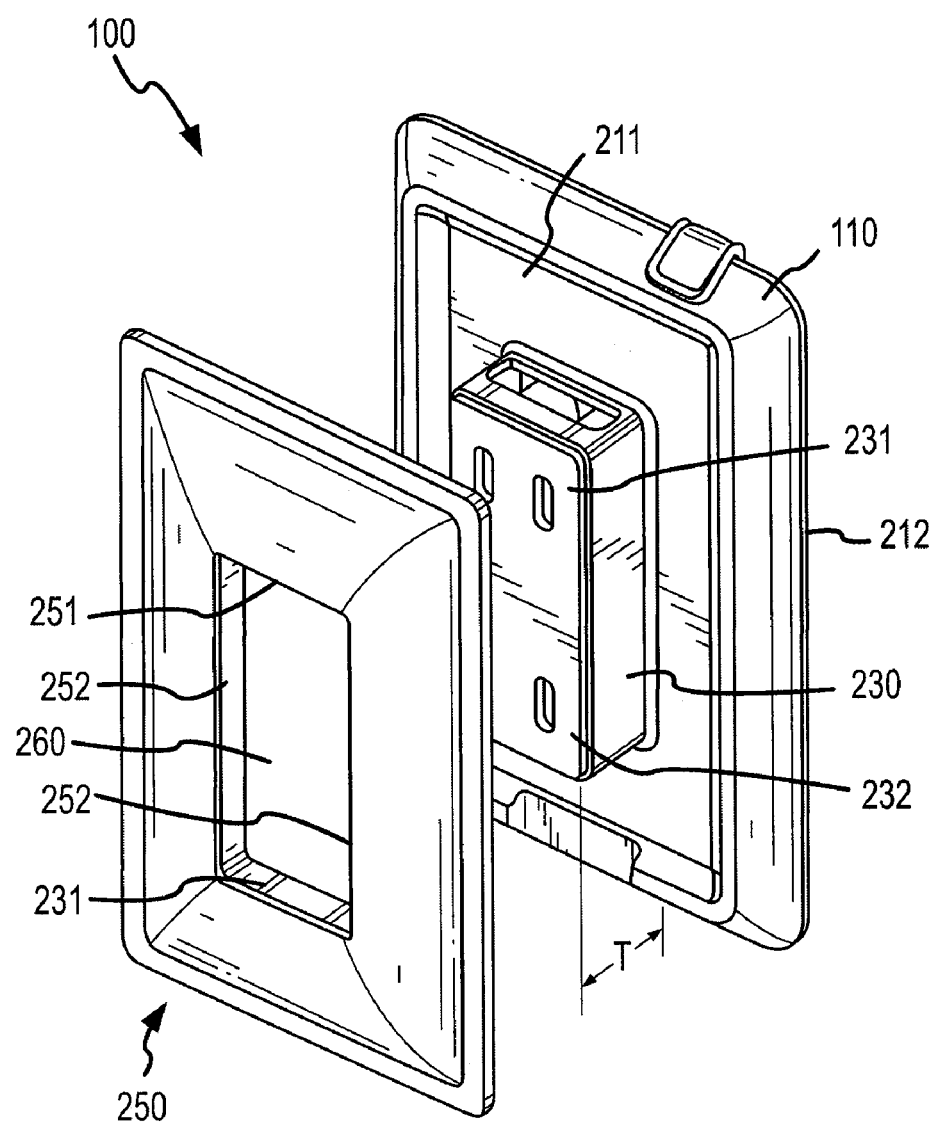
FIGS. 4A-B are perspective views of an exemplary embodiment of a housing and refill in accordance with the present invention.
Figure 4B:
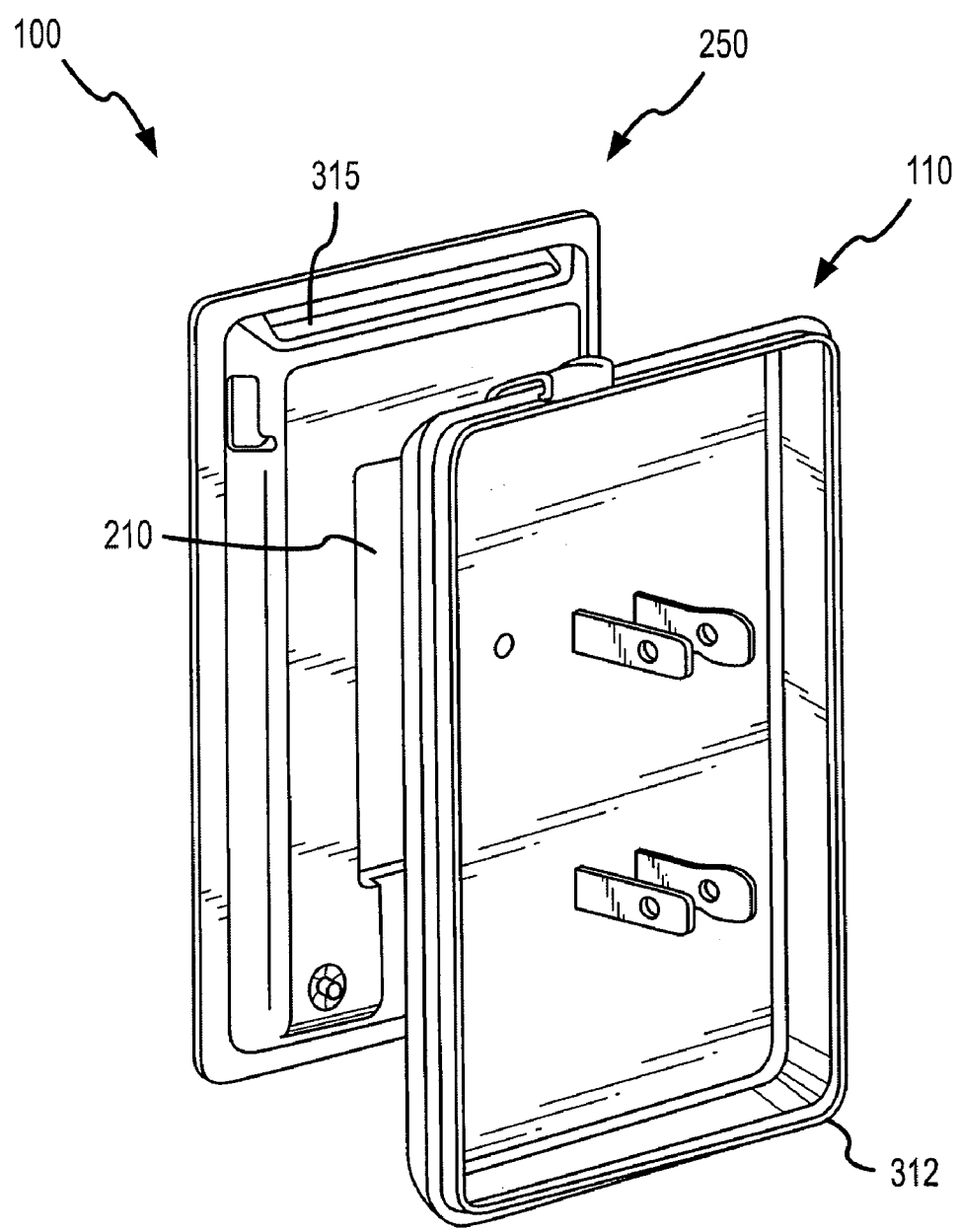

Additionally, in accordance with various embodiments and with particular reference to FIGS. 4A-B, vapor-dispensing device 100 further comprises a refill 250 (e.g., a fragrance refill) which suitably interconnects with housing 110 in an assembled form. Briefly, however, it is worth noting that in accordance with various alternative embodiments of the present invention, vapor-dispensing device 100 may comprise any number of structures, including comprising a single, unitary structure. For example, while the presently described embodiment comprises housing 110 which serves to facilitate connection to the wall outlet and heating of the material provided in refill 250, in various other embodiments, housing 110 and refill 250 might have different roles, i.e., they may act cooperatively to provide heat for volatilization and/or fragrance and heating elements may be reversed on the structures. Further still, alternatively, device 100 may comprise a single, unitary structure with all vaporization elements integrated into one unit. For example, in various non-limiting embodiments, device 100 may comprise the wall outlet itself; that is, device 100 may take the place of the wall plug device and faceplate and be integrated with the wall.

That being said, in the presently described embodiment, housing 110 suitably further comprises an outlet structure 230 substantially centrally located on front surface 211. Generally speaking, outlet structure 230 is a block-like configuration of built up material for, as described below, receiving refill 250. Additionally, in accordance with various embodiments of the present invention, outlet structure 230 surrounds electrical outlets 231, 232, which are preferably located in a substantially similar location as the outlets of a standard wall outlet. Outlet structure suitably facilitates the interconnection of housing 110 and refill 250, as well as, in various instances, the ability to provide power to other devices through outlets 231, 232.

In the present exemplary embodiment, outlet structure 230 extends from front surface 211 a distance of about 5 cm, though this is merely exemplary and any value may be chosen such that a low-profile nature of device 100 is maintained. Similarly, outlet structure 230 may be suitably configured in any number of shapes and likewise may comprise any number of distinct projecting structures. For example, in the presently described embodiment, outlet structure 230 comprises one structure which surrounds both outlets and has a substantially rectangular shape with rounded corners. However, outlet structure 230 may also comprise many variants of shapes. For example, outlet structure 230 may be suitably configured with an "hour-glass," "circular," or "triangular" configuration or the like. Similarly, rather than outlet structure comprising one unitary structure surrounding both outlets, outlet structure 230 can comprise two or more separate and distinct structures, each surrounding another outlet. Likewise, those separate structures themselves can have any number of configurations and shapes. Moreover, outlet structure 230, as shown in the illustrated exemplary embodiment, need not have any outlets but rather may simply cover the wall outlets.

Now, in accordance with the presently described illustrative embodiment, refill 250 is suitably configured with a shape and size such that it can be assembled to housing 110 in a manner which facilitates the minimizing of the likelihood of being noticed by those in the vicinity of vapor-dispensing device 100. For example, in the present exemplary embodiment, refill 250 has a substantially rectangular shape corresponding to housing 110 (similar to a standard wall outlet plate).

Figures 5A, 5B:
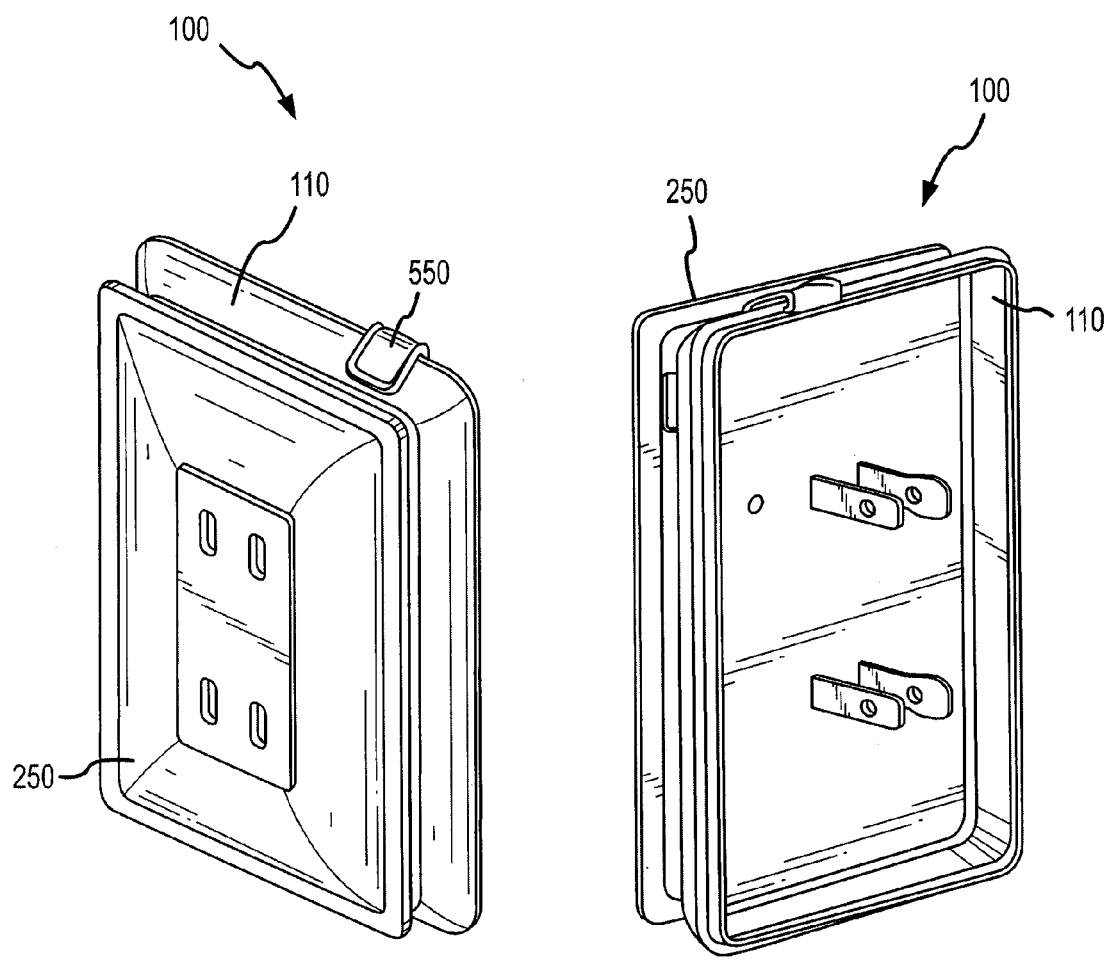
FIGS. 5A-B are perspective views of the assembled housing and refill of FIGS. 4A-B.
Figure 6:
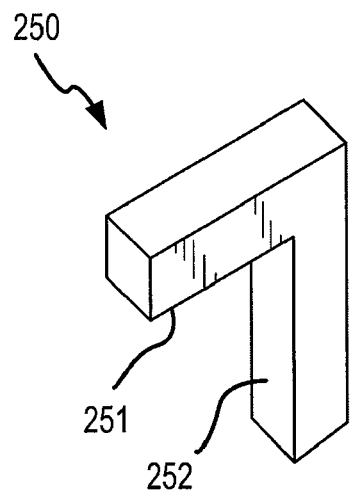
FIGS. 6-8 are perspective views of various exemplary alternative refills in accordance with the present invention.
Figure 7:
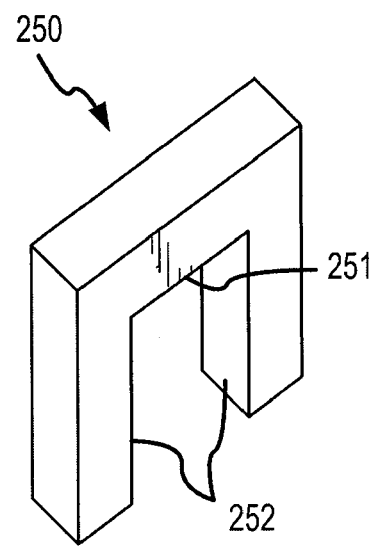
Figure 8:
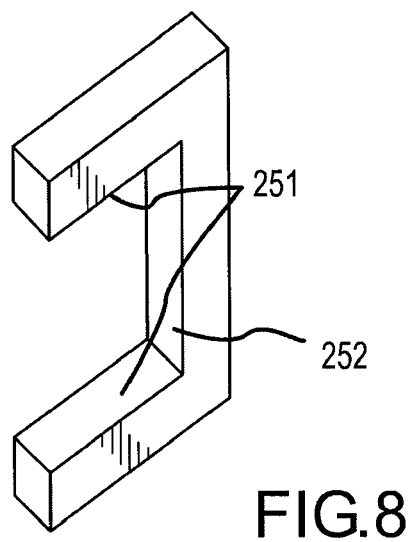

In accordance with various embodiments of the present invention, refill 250 has a configuration typically having at least one lateral support surface 251 and at least one longitudinal support surface 252 for stabilizing, guiding and/or retaining of refill 250. For example, in the embodiment illustrated in FIGS. 4-5, refill 250 comprises an aperture 260 to facilitate connection to housing 110. In this exemplary embodiment, aperture 260 extends all of the way through refill 250, though in various alternate embodiments, to facilitate the above-mentioned interconnection, aperture 260 may only extend partially through refill 250. Preferably, aperture 260 is of substantially the same size as outlet structure 230. Thus, in accordance with various embodiments of the present invention, refill 250 can be placed over outlet structure 230 to form the assembled vapor-dispensing device 100 of FIGS. 5A-B. Thus, the presently described embodiment of refill 250 has two lateral support surfaces and two longitudinal support surfaces. That is, as in the above described embodiment, the portions above and below aperture 260 act as lateral support surfaces 251 and the portions to the right and left of aperture 260 act as longitudinal support surfaces 252. However, other embodiments having similar support surfaces are contemplated in accordance with the present invention. For example, with reference to FIGS. 6-8, refill may have an "L-shape" (FIG. 6), a "horseshoe" shape (FIG. 7), a "C-shape" (FIG. 8) or any number of alternative shapes having the support described herein.

Further, in accordance with various aspects of the presently described embodiment, refill 250 may have various features. For example, refill may include various indicators for determining the "state" of refill 250. In one context, indicators comprise a "use cue" which indicates the amount of volatizable material left in refill 250. Alternatively, "use cue" may provide the ability to determine which volatizable material (e.g., in embodiments containing more than material) is currently being dispensed.

Figure 9:
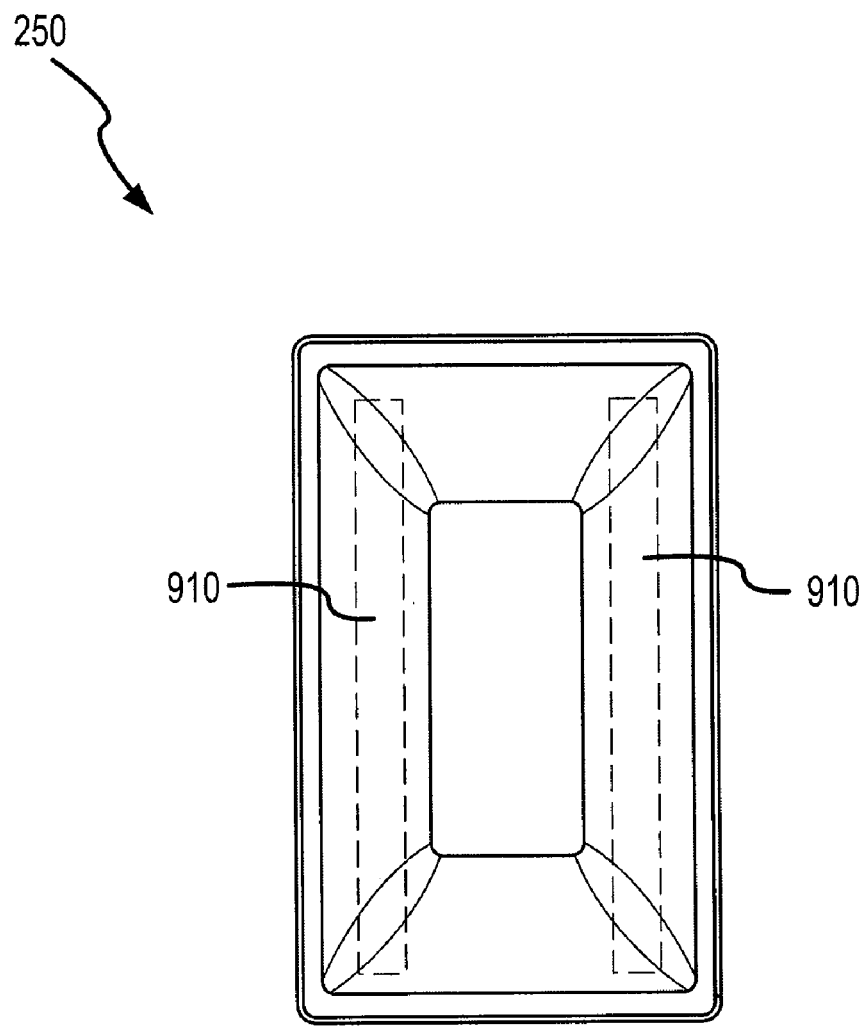
FIG. 9 is a front view of a refill with an indicator in accordance with the present invention.

For example, in accordance with various aspects of the presently described embodiments and with reference to FIG. 9, refill 250 comprises use cue in the form of a translucent to clear window 910, comprising anywhere from a portion of refill 250 to the entirety of refill 250. Window is preferably located longitudinally coincidental with refill 250 such that the amount of material within refill 250 can be observed from an empty to near empty state, to a full to near full state. Similarly, in accordance with alternative aspects of use cue, the indicator may comprise a level which moves up and down refill 250 in a manner corresponding to the amount of material present in refill 250. Such embodiments may embody floats and corresponding gauges similar to those found in fuel tanks.

That being said, in any event, it should thus be appreciated a refill in accordance with the present invention may be suitably configured to have a number of indicating aspects now known or as yet unknown.

In this regard, while the illustrated embodiment is characterized by a generally rectilinear shape, it will be understood that the present invention is not so limited. In various exemplary embodiments, the front 211 and back 312 surfaces may be different in height and width from each other, and/or from the electrical receptacle 160. Similarly, in accordance with various embodiments of the present invention, device 100 has a generally discrete nature often having exemplary features such as having symmetry within and without the faceplate to which device 100 is inserted, having corners blend into the wall to which device 100 is attached, or otherwise mimic typical standard wall outlets. These and other features are described in the U.S. patent applications mentioned and incorporated by reference above.

In accordance with various exemplary embodiments of the present invention, vapor-dispensing devices 100 include various activating mechanisms which cause such devices to begin dispensing fragrance, release dispensing fragrance, increase or decrease dispensation and/or change the dispensation of the fragrance (or other material to be delivered).

For example, in various exemplary embodiments of the present invention, the housing may be configured to facilitate heating of a volatizable material provided by fragrance delivery system 120. Housing 110 may comprise a heating element that suitably assists in vaporizing the volatizable material from fragrance delivery system 120. In this embodiment, the heating element may comprise a resistance-type heating element, preferably of a printed-substrate circuit, though generally speaking, any mechanism that assists in volatizing the material from fragrance delivery system 120 may, typically through kinetic energy, be a "heating element". Additionally, momentarily, it should be noted, that in various alternative embodiments of the present invention, vapor-dispensing device 100 may be a "passive" vaporizer. Stated otherwise, the material of fragrance delivery system 120 may volatize merely by exposure to ambient conditions (e.g., room temperature). Thus, no heating element may be required. Fragrance delivery system 120 may also comprise other material delivery systems such as, for example, gel and/or membrane type fragrance dispensers. In such cases, the volatizable material might be in a "gel" and/or semi-permeable solid form that dispenses through mechanisms such as sublimation. Thus, it should be appreciated that any fragrance delivery mechanism now known or as yet unknown in the art can suitably be configured to be used in the present invention.

Heating elements may be suitably configured to be adjustable to varying temperatures. In accordance with various aspects of the present invention, a switch may also be suitably configured to control the varying temperature of a heating element and/or provide the ability to turn the unit ON and OFF. For example, with momentary reference back to FIG. 5, in one exemplary embodiment of the present invention, switch comprises a slide-type control 550. Similarly, dispensers having variable temperature control can provide the ability to increase or decrease the amount of fragrance dispensed depending on the intensity and strength of heat provided by heating element, user desired performance, room size and the like.

Alternative embodiments of the present invention, activating mechanisms which cause vapor-dispensing devices to begin dispensing fragrance or cease dispensing fragrance, increase or decrease dispensation of fragrance and/or change the fragrance.

For example, in one exemplary embodiment of the present invention, device 100 may be configured with a timing device which activates device 100 at pre-determined intervals. For example, in the context of an in-home use, timer may be suitably set to activate device 100 when people are most likely to be in the vicinity of device 100. Timer may comprise any suitable (e.g., known or as yet unknown) analog or digital-type chronometer for keeping track of time and which is capable of activating and/or deactivating, at pre-determined intervals.

Thus, when such timing devices are used, while people are at work (e.g., from morning until evening), timer may be set to activate device 100 when they are expected home (evening), and deactivate device 100 when they are expected to leave (morning). In this regard, benefits such as fragrance conservation, extending the life of device 100 and/or reducing or preventing unneeded build-up of the volatized material are provided.

Similarly, device 100 may also be configured with a variety of altered environment detectors which selectively activate various components of device 100 under a variety of pre-determined circumstances. Such detectors generally include any of various photo-, infrared- or other cell-type detectors which are capable of detecting motion, heat, light or other changing conditions. For example, in one exemplary embodiment of the present invention, a motion or heat sensor which senses the presence or lack thereof of people (or other living beings) in proximity to device, may be integrated with device 100. In this context, when sensor does not detect the presence of people, sensor deactivates device 100; when sensor senses people, sensor activates device 100. Thus, when a person moves into proximity with device 100, device 100 will be activated and dispense fragrance (or other volatizable material, such as, in the case of animals, a deodorizer). When sensor no longer detects a person in proximity to device 100, device 100 is deactivated, again conserving fragrance or preventing unneeded build-up of the volatized material.

Vapor-dispensing devices 100 containing detectors in accordance with the present invention may have additional aspects or uses as well. For example, detectors may comprise sensors which activate other auxiliary devices, appliances or the like, either in conjunction with, or separate from device 100 itself. For example, sensors may activate a light separate from (such as a table lamp) or integrated with (such as a built-in "nightlight") device 100 when motion in proximity to device 100 is detected. In any event, it should be apparent that the foregoing are merely exemplary, and as such, are examples of alternative aspects of the present invention which cause activation/deactivation of device 100 and/or auxiliary aspects of device 100 depending on changes in the ambient environment surrounding it. Accordingly, other aspects along such lines and falling within the scope of the present invention are potentially limitless in nature.

In various exemplary embodiments, vapor-dispensing device 100 is suitably configured with other improved features. For example, various benefits may be realized through optimized selection of wicking materials for fragrance delivery system 120. For example, in the present exemplary embodiment, fragrance delivery system 120 comprises wicking structure (such as that illustrated in FIG. 10) in communication with an eminator pad having an enlarged surface area and configured from a porous material. For example, eminator pad (and as described below, various wicks) may comprise materials including nylon, porous plastics, various natural and synthetic fibers or other suitable materials, generally being characterized by having pore sizes in the range of about 10 to about 30 microns and void volume ratios of about 30% to about 40%, such that fragrance delivery from pad 410 ranges from about 15 mg/hr to 25 mg/hr at 50 degrees Celsius and about 35 to about 45 at 60 degrees Celsius. It should be appreciated, however, that alternative materials, pore sizes and void volumes may be selected depending on the desired fragrance delivery ranges are obtained for given temperatures.

Figure 10:
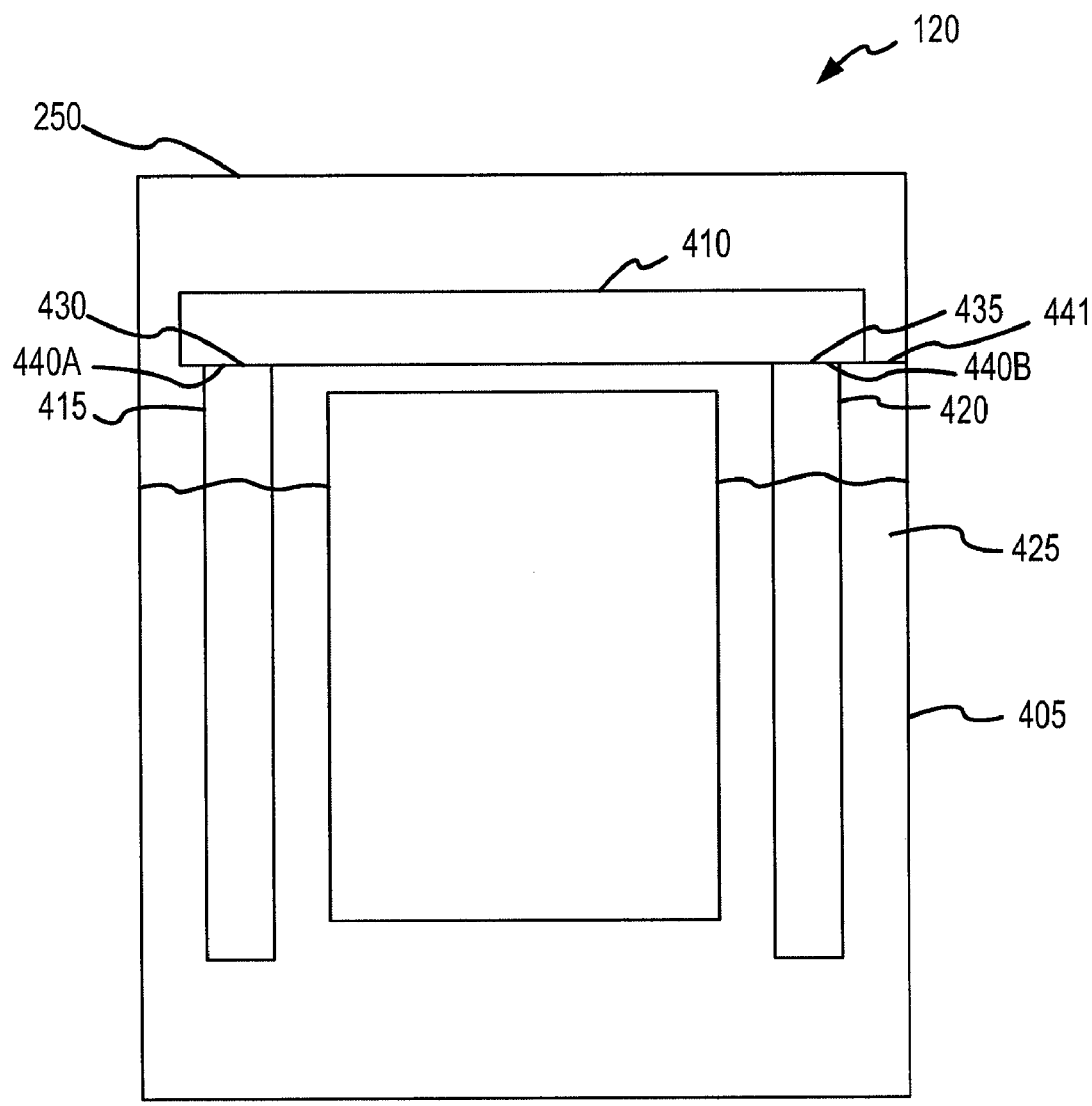
FIG. 10 is a perspective view of an exemplary fragrance delivery system in accordance with the present invention.

Additionally, in various exemplary embodiments of the present invention, the physical configuration and components of fragrance delivery system 120 may also provide improved fragrance delivery. For example, FIG. 10 illustrates an exemplary fragrance delivery system in accordance with the present invention. Fragrance delivery system 120 comprises a chamber 405, an eminator 410, and first and second wicks 415, 420 ("noodles"). In this embodiment, chamber 405 is configured to contain a volatizable material 425 contained therein. For example, chamber 405 may be configured as a liquid filled reservoir, which is functionally similar to the reservoir bottles of now known vaporizer refill bottles. In such configurations, chamber 405 has a hollow section filled with, for example, a scented oil that is vaporized from fragrance delivery system 120.

Eminator 410 is configured to receive volatizable material 425 and to facilitate the dispersion of said material to the surrounding environment. For example, as described above, eminator 410 may draw volatizable material into a region that can be heated by a heating element. Eminator 410 may be configured to be proximate to a first point 430 on first wick 415 and to a second point 435 to second wick 420 such that material 425 can transfer to eminator 410. For example, in many embodiments such proximity may require actual contact, though it should be understood that in various other embodiments, "proximity" encompasses non-contact, where eminator 410 and wicks 415, 420 are near enough to facilitate material 425 transfer. In this manner, eminator 410 receives volatizable material 425 through such mechanisms as the wicking of volatizable material 425 from chamber 405. As mentioned above, in various embodiments, first and second wicks 415, 420 may be made, for example, of a porous material such as graphite, porous plastic or other fibrous materials. Additionally, in various embodiments, multiple chambers, each containing a distinct material, may be provided for dispensing a different (or additional) volatizable material and is suitably accessed by each wick.

Similarly, the shape and/or size of fragrance delivery system 120 may change fragrance delivery characteristics. For example, in the presently described embodiment, eminator 410 preferably has an area configured to absorb and transport material 425 evenly over its surface. In this exemplary embodiment, the area of eminator 410 is selected based upon characteristics including, among others, fluid transfer rates from wicks 415, 420, the rate at which material 425 wicks through eminator 410, the rate at which material 425 volatizes from eminator 410 and the like.

In the presently described embodiment, using a liquid scented oil, eminator 410 is rectilinear, having a length (l) of about 6 cm and a height (h) of about 1.5, giving eminator a total surface area (including both sides of eminator 410) of about 9 sq. cm. In the same embodiment, wicks 415, 420 have generally rectilinear shapes as well, having lengths (l) of about 10 cm and widths (w) of about 0.5 cm.

It will be appreciated that with various alternative embodiments of the present invention, fluid transport system 120, eminator 410 and/or wicks 415, 420 may have other than rectilinear shapes (and still have the same surface area) and likewise, may have similar shapes, but different surface areas, yet still fall within the ambit of the present invention.

Figure 16:
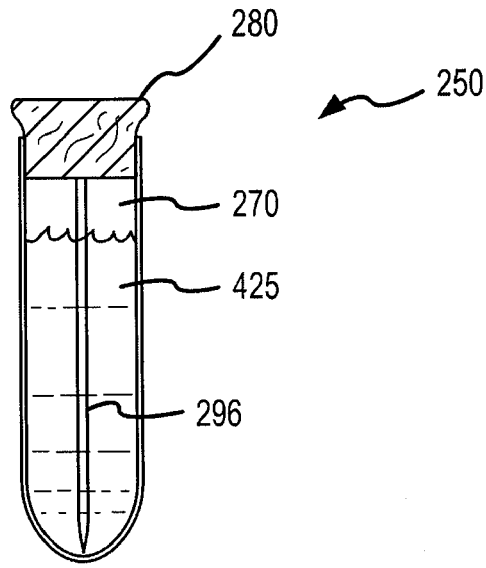
FIG. 16 is a front view of an exemplary embodiment of a refill in accordance with the present invention.
Figure 17A:
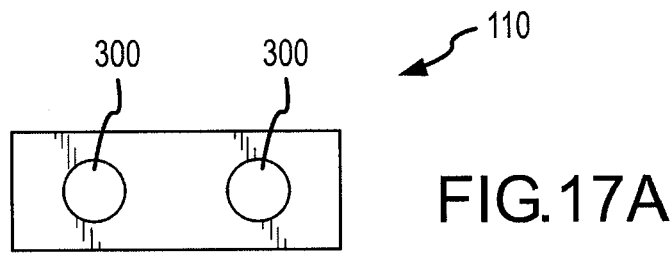
FIGS. 17A-B are top and front views of an exemplary embodiment of a device housing for use with the refill illustrated in FIG. 16 in accordance the present invention.
Figure 17B:
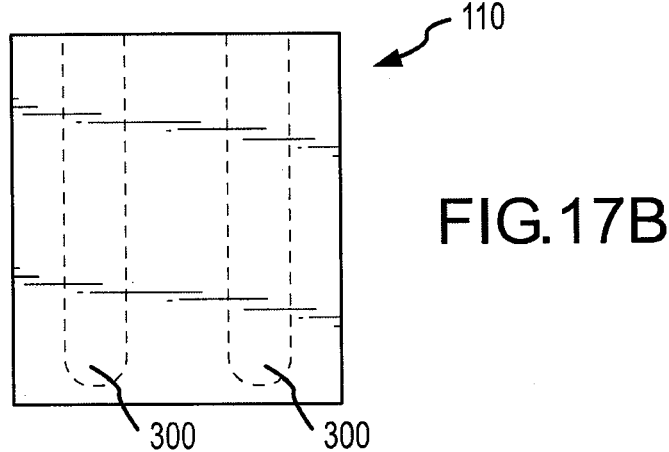

For example, FIG. 16 shows an alternative fluid transport system in accordance with the present invention. In this embodiment, refill 250 comprises a "tube" like reservoir 270 for containing material 425. Tube is configured to be placed in housing 110 of device 100, which in various embodiments, allows easy refilling of the device 100 and/or facilitates control of intensity, for example, through adding varying numbers of tubes to housing 110. For example, FIG. 17 illustrates an exemplary housing 110 configured for retention of refills in tube shaped recesses 300. As illustrated, housing 110 is suitably configured for retention of two refills, though it should be apparent that housing 110 may be configured with additional or fewer recesses 300 depending on various applications of device 100. Similarly, regardless of the number of recesses 300, such configurations may have additional benefits of allowing a user of device 100 to vary the number of refills placed in housing 110 to vary, among other aspects, intensity/amount of material 425 diffused. Additionally, as described in more detail below, various re-sealable access mechanism may be provided which can be opened for insertion of refills, and closed once refills are inserted.

In various exemplary embodiments, a stopper 280 is provided for maintaining material 425 in reservoir 270. Stopper 280 is preferably comprised of a material capable of transporting material 425 to the environment surrounding refill 250, thereby performing similar to eminator 410 in the embodiment described above. In the a preferred embodiment, stopper 280 comprises a plug-like element formed from porous plastic, though any number of now known or as yet unknown materials, typically having void volumes and pore sizes selected as described above may likewise be substituted. Additionally, with momentary reference to FIG. 18, stopper comprises a plurality of "fins" compressed together. Similar to the porous plastic plug, fins suitably allow the transport of material 425 from reservoir to the ambient environment where material is volatized.

Figure 19:
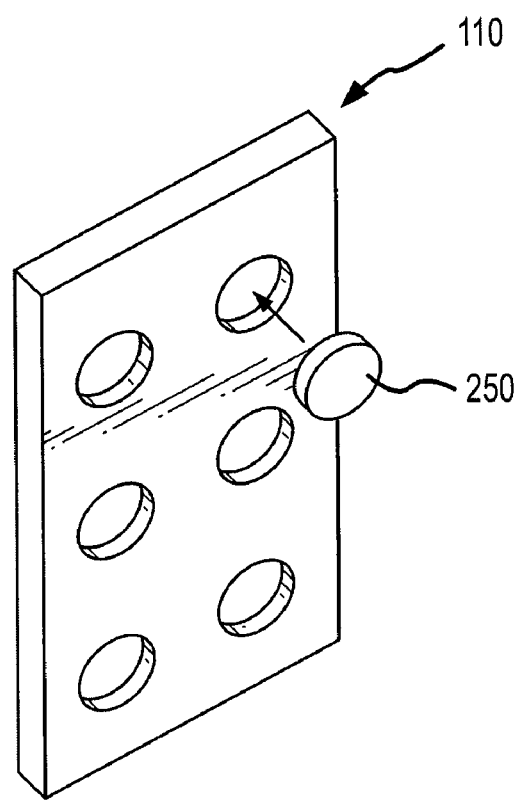
FIG. 19 is a perspective view of another exemplary embodiment of a refill and housing in accordance with the present invention.

In accordance with another aspect of the present invention, refills 250 may comprise other retaining vessels for containing material 425. For example, with reference to FIG. 19, refills 250 comprise puck shaped vessels. In this embodiment, pucks 250 contain a gel type air freshener, though, in various alternative embodiments, pucks 250 may contain various others forms of material 425. Similar to the embodiments described above, housing 110 is configured to receive one or more of pucks 250, and, as described above, may allow a user to select the number of pucks 250 placed in device 110 to, among other things, control intensity and amount of material 425 dispersed.

It should thus be appreciated that refills 250 generally comprise many known or as yet unknown configurations which are capable of retaining a material to be volatized (e.g., gel, liquid, oil, etc.), yet allowing passage as desired to a surrounding environment.

Figure 18:
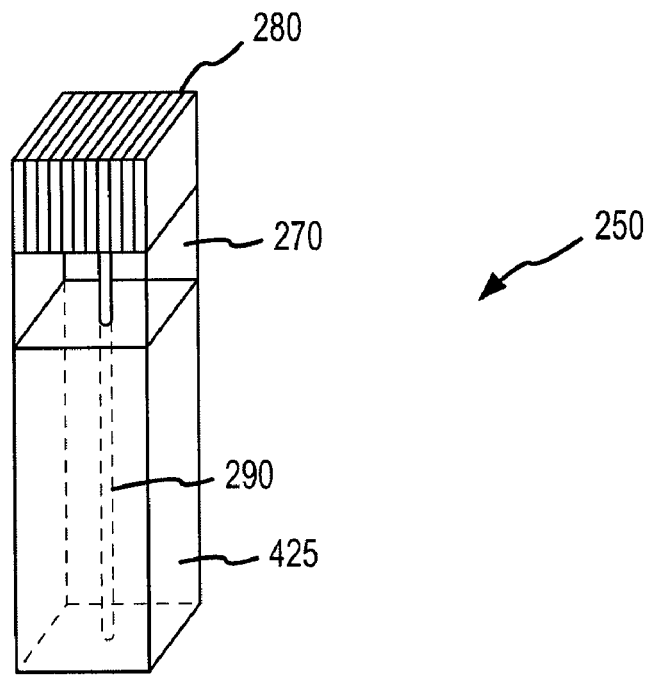
FIG. 18 is a perspective view of another exemplary embodiment of a refill in accordance with the present invention.

In accordance with various embodiments, and with exemplary reference to FIGS. 16 and 18, one or more dip sticks 290 is provided for assisting in the transport of material 425 to stopper 280, similar to wicks 415, 420 described above. In the presently described embodiment, dip stick 290 has a thin, string-like configuration which transports material 425 to stopper 280.

Optionally, in various exemplary embodiments, in the context of activation/deactivation of device 100, a transport inhibitor may be provided for preventing volatizable material 425 from passing from chamber 405 to eminator 410 (e.g., via wicks 415, 420) until a desired or proscribed time. For example, prior to use of device 100 (e.g., during shipping or storage), it is often desirable to limit or prevent the transfer of volatizable material 425 between to eminator 410. In accordance with the present optional aspect of the invention, a structure comprised of a material impermeable to volatizable material 425 prevents the passage of material 425 from passing to either wicks 415, 420 (and thus to eminator 410) and/or to eminator 410. For example, the impermeable structure prevents contact between eminator 410 and wicks 415, 420, for example at contact points 430, 435, thereby preventing the passage of material 425 from chamber 405 to eminator 410 via wicks 415, 420. However, when the structure is removed, contact between eminator 410 and wicks 415, 420 occurs and transfer of volatizable material 425 likewise can occur. Similarly, it should be appreciated that placing the impermeable structure directly between wicks 415, 420 and the actual material 425 in chamber 405 likewise ultimately prevents the passage of material 425 to eminator 410.

In the presently described exemplary embodiment, the impermeable structure comprises a "rip-cord" device 440A, 440B which is impermeable by volatizable material 425 (e.g. plastic, metal foil or the like) is placed at contact points 430, 435. Rip-cord 440A, 440B comprises a protrusion (441), such as a grasping tab, which can be grasped by the user and pulled clear of fragrance delivery system 120, thereby allowing the passage of material 425 to eminator 410. It should be appreciated that in its various embodiments, multiple rip-cords may be needed, generally determined by the number of contact points and/or ideal placement of structure for blocking the passage of the volatizable material. Additionally, in accordance with various embodiments, rip-cords may be removed by a number means, including one protrusion for grasping which removes all rip-cords, or multiple protrusions, depending on which rip-cords are intended to be removed.

Similarly, in embodiments where rip-cords are selectively removed, benefits including a choice of dispensation of volatizable material can be realized by the removal of the selected rip-cord. For example, in the context of a fragrance vaporizer, multiple scents may be dispensed depending on the choice. Likewise, after the vacating of one chamber has occurred, device 100 can have continued use by the removal of another rip-cord, thereby providing passage of volatizable material from another chamber.

In accordance with another aspect of the present invention, as mentioned briefly above, the configuration of housing 110 and/or refill 250 may allow selective access to facilitate the placement of refill 250 in housing 110 and/or provide access to transport inhibitor. For example, with reference to FIGS. 11A-C, refill 250 further comprises access to transport inhibitor through a door 251 connected to refill 250 by hinge(s) 252. In this embodiment, door 251 is proximate to transport inhibitor (rip-cords) such that when door 251 is opened, rip-cords are accessible for removal. Optionally, door 251 is proximate to eminator 410 (as in the illustrated embodiments), thereby providing further benefits such as exposure to the environment. Further still, with reference to the same FIGS., when door 251 is in an open position, refills 250 are suitably insertable/removable.

Further, door 251 may provide easier access for the purpose of filling refill 250. For example to fill, door 251 is opened and volatizable material is inserted into refill 250. Additionally such access may also provide the ability to ensure proper placement of wicks and eminator, as discussed above.

Further still, in embodiments similar to those described above, door 251 may provide further features relating to activation and/or safety. For example, the opening or closing of door 251 may selectively close the circuit containing the heating element. For example, the opening or closing of door 251 may selectively close the circuit containing the heating element. For example, closing door 251 may close the circuit, thereby allowing heating element to be activated; thus, heating element would only operate when closed, thus improving safety.

Lastly, it should be noted that though access is provided through a "door" in the embodiments discussed above, any mechanism which provides such access, and not necessarily a "door" in its ordinary context falls within the meaning of "access" in the context of the present invention.

In accordance with still another aspect of the presently described embodiment, orientation of wicks 415, 420 suitably provide the ability for fragrance delivery system 120 to operate in multiple/non-standard positions. For example, as can be gleaned from the embodiment illustrated in FIG. 10, in the vertical position shown, wicks 415, 420 allow passage of volatizable material 425 upwards to eminator 410. However, in non-vertical positions, such as where the outlets into which vapor-dispensing device 100 is plugged is not oriented vertically, wicks 415, 420 still remain in substantial contact with volatizable material 425, thus still providing the passage of volatizable material 425 to eminator 410, thereby allowing fragrance delivery system 120 to operate in a variety of non-vertical positions.

In accordance with the presently described illustrative embodiment, fragrance delivery system 120 is suitably configured to have the shape and size of housing 110 such that it can be assembled to housing 110 in a manner that facilitates the minimizing of the likelihood of being noticed by those in the vicinity of vapor-dispensing device 100. For example, as described above in the present exemplary embodiment, fragrance delivery system 120 has a substantially rectangular shape corresponding to housing 110 (similar to a standard wall outlet plate). Additionally, the presently described embodiment may suitably exhibit improved stability, and/or facilitate the interaction of heating elements (to the extent that heating elements are included in vapor-dispensing device 100) with fragrance delivery system 120.

Figure 12:
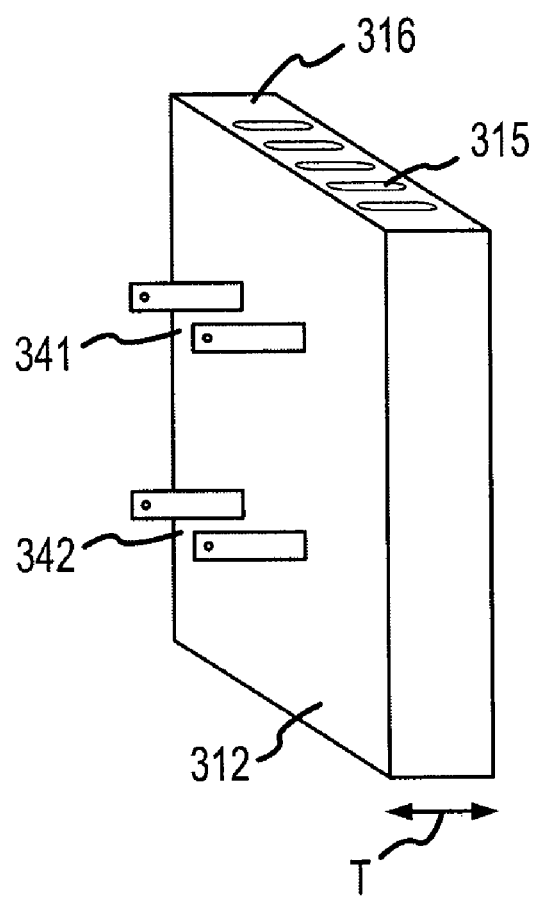
FIG. 12 is a perspective view of another exemplary embodiment of the present invention.

In accordance with further aspects of the present invention, benefits may be obtained through the configuration of device 100 itself, for example, through the addition and configuration of vents on housing 110, refills for device 100 and/or other components of device 100. For example, with momentary reference to FIGS. 4B and 12, housing 110 is suitably configured with vents 315 which allow passage of volatilized fragrance from device 100. In this exemplary embodiment, vents 315 are preferably located in proximity to an emanating pad (or other fragrance deliverer) on an upper surface 316 of housing 110. However, it should be appreciated that in alternative embodiments, vents 315 may be situated on other components of device 100, particularly, in cases where the fragrance is emitted elsewhere on device 100. For example, in some instances, fragrance may be emitted directly from refill units for device 100, and to facilitate the same, vents 315 are located on such refills.

Accordingly, vents in accordance with the present invention may take a number of configurations, and may provide various benefits, including improved dispensation of fragrance from device 100 through mechanisms including faster fragrance transport to the ambient environment.

In accordance with another exemplary embodiment of the present invention, additional fragrance dispensation improvements may be obtained through fragrance boosting mechanisms used with or without improvements to vents and fragrance delivery systems. In this context, fragrance boost mechanisms generally comprise structure which improves fragrance dispensation into the ambient environment under circumstances including improved or heightened steady delivery over time and/or one-time fragrance intensifying "boosts."

For example, in accordance with an exemplary embodiment of the present invention, fragrance boosting mechanism may comprise a fan, which upon activation, increases air flow in the vicinity of fragrance deliver system 120, thereby increasing the dispensation of fragrance from device 100. In accordance with various aspects of such embodiments, the fan may be selectively operated to increase fragrance dispensation. For example, through use of an ON/OFF switch, when switched to an "ON" position, the fan is active, thereby increasing fragrance dispensation for sustained intervals. Alternatively, the fan may be turned ON briefly, for momentary boosts in the intensity of fragrance dispensed. Optionally, in connection with various exemplary embodiments, fan may be activated by the aforementioned altered environment detectors (e.g., motion sensors) when environment altering conditions (e.g., people present near device 100) occur.

In accordance with alternative embodiments of the present invention, "boosting" may occur through alternative mechanisms. For example, use of a transport mechanism may nearly instantly release an increased amount of fragrance. Such mechanisms may comprise pressurized, aerosol type mechanism built in to device 100, which, when activated propel a substantially instantaneous burst of fragrance. Such aerosol device are typically powered by a pressurized container which ejects from fragrance (e.g., from a main fragrance reservoir of device or an alternative, supplemental reservoir) into the ambient environment. However, alternatively, rather than using a pressurized container, the transport mechanism may comprise a mechanical type pump and spray apparatus (such as those known in the art) which transports fragrance from a reservoir by mechanical activation (e.g., pressing a pump). In any event, it should be appreciated that any device now known or as yet unknown, and variations of the same, which is capable of momentarily delivering a burst of fragrance falls within the scope of the present invention.

Housing 110 may be configured in various ways for attachment to electrical receptacle 160. In an exemplary embodiment of the present invention, housing 110 is configured to be attachable to electrical receptacle 160 via one or more plugs (e.g., plugs 141 and 142 shown in FIG. 1). For example, with reference back to FIGS. 3-5, a first plug 341 is suitably configured to extend from the back surface 312 of housing 110. A second plug 342 may also be configured to extend from the back of surface 312. In this illustrated embodiment, first and/or second plug(s) 341 and 342 comprise conventional (and/or standardized) two prong plug(s) configured to be inserted into a standard duplex electrical receptacle. In general, however, the plugs may comprise any suitable male or female component (whether electrically functional or non-functional) configured to interface with corresponding structure within electrical receptacle 160.

Housing 110 may also be attached to electrical receptacle 160 via a suitable fastener (e.g., a conventional screw) located, for example, at the center or ends of the electrical receptacle. In another example, clips, Velcro brand fasteners, snaps, and/or the like may be suitably used to attach housing 110 to electrical receptacle 160.

Device outlets 131 and 132 are generally configured to mirror the functionality provided by the type (or types) of outlets 171 and 172 disposed within receptacle 160. The use of device outlets 131 for electrical needs thereby increases the inconspicuousness of vapor-dispensing device 100. For example, the illusion that vapor-dispensing device 100 is merely a typical outlet is maintained by allowing other devices (e.g., lamps, televisions, clocks, etc.) to be plugged into the same outlet. For example, outlets 171 and 172 may correspond to standard two-pronged electrical AC outlets found in many homes. In this case, it may be advantageous to likewise configure housing 110 to include standard two-pronged electrical outlets 131 and 132 which substantially correspond in location in geometry to that provided by receptacle 160.

Device outlets 131 and 132 may be electrically coupled to corresponding outlets 171 and 172, or may configured with any suitable electrical topology that provides the desired functionality of device 100. For example, a single plug 141 may be configured to be electrically coupled to more than one device outlet (e.g., 131 and 132) in housing 110. Furthermore, additional plugs may be configured, in various combinations, to be electrically coupled to one or more device outlet(s). In one exemplary embodiment of the present invention, first plug 341 is configured to provide power from first receptacle outlet 171 to two or more device outlets (e.g., 131 and 132). In another exemplary embodiment of the present invention, first plug 341 is configured to provide power from receptacle outlet 171 to first device outlet 231, and second plug 342 is also configured to provide power from receptacle outlet 172 to device outlet 232.

An exemplary beneficial aspect of the above-described embodiments having functional outlets includes the ability to stack dispensing devices. That is, as each unit mimics the outlet unto which it is connected, additional devices can be plugged into already inserted devices, thereby providing the ability to stack the devices and, among other things, obtained enhanced delivery of the material to be dispensed, create combinations of material to be dispensed and the like.

Alternatively, one or more plugs may be non-functional (or "dummy" plugs). Such non-functional plugs, which may comprise any suitable plastic or other insulating material, may provide structural support of the vapor-dispensing device. Alternatively, a metallic material may be used for the non-conducting plugs to the extent that the non-functional plug is configured such that a circuit is not formed by that plug.

Figure 13:
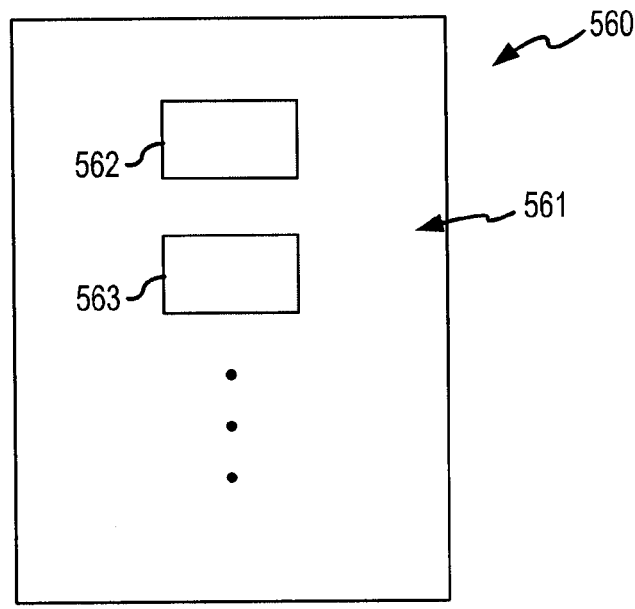
FIGS. 13-15 are front views of faceplates used in accordance with various embodiments of the present invention.

As mentioned above, electrical receptacle 160 may include any standard wall outlet fixture configured for receiving electrical plugs, such as plugs provided on one end of a power cord. In the above-described embodiments, electrical receptacle 160 comprises two or more outlets 171 and 172. For example, FIG. 13 illustrates an exemplary electrical receptacle 560 comprising a face plate 561 and two or more outlets (e.g., 562, and 563). Face plate 561 may comprise openings suitable for exposing one or more outlets. Various styles and designs of face plates may be used.

Figures 14, 15:
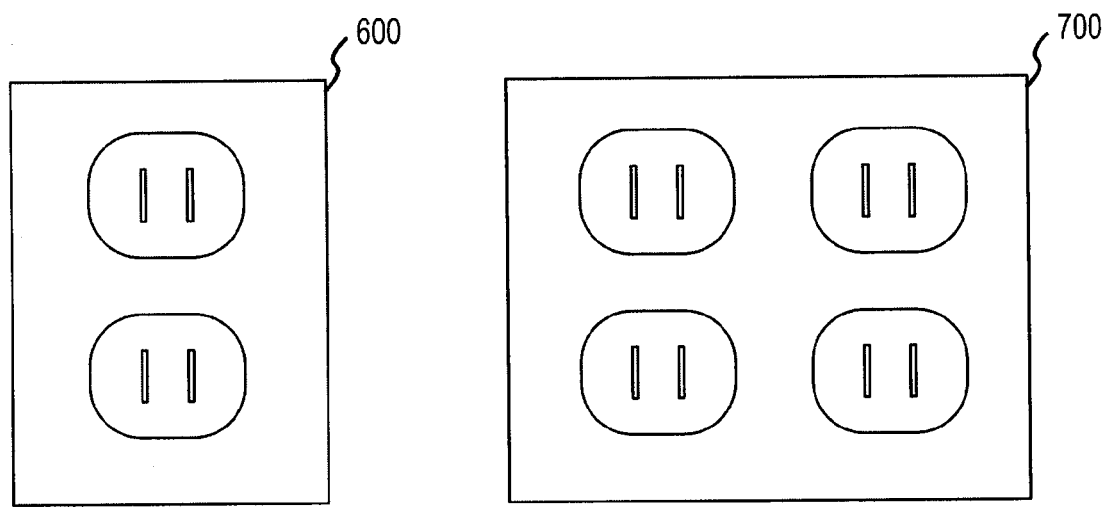

Electrical receptacle 160 may also comprise various numbers of outlets. With reference to FIG. 14, an exemplary dual outlet electrical receptacle 600 is illustrated. With reference to FIG. 15, an exemplary four outlet electrical receptacle 700 is illustrated. Other outlet numbers and arrangements may suitably be used. The number of device outlets 131 may not correspond to the number of electrical receptacle outlets provided on the housing. For example, two electrical receptacle outlets may be covered and four device outlets provided for use. Thus, vapor-dispensing device 100 may serve as an adapter splitting one plug into two or more device outlets.

In accordance with additional aspects of various embodiments of the present invention, an electrical device for insertion into an electrical receptacle which is capable of adapting to receptacles of varying sizes and dimensions. Briefly, as used herein "adaptive" refers to the ability to adjust to fit a differently sized or spaced receptacle, and as such, shall be synonymous with "adjustable" and other like meaning terms.

Figure 20:
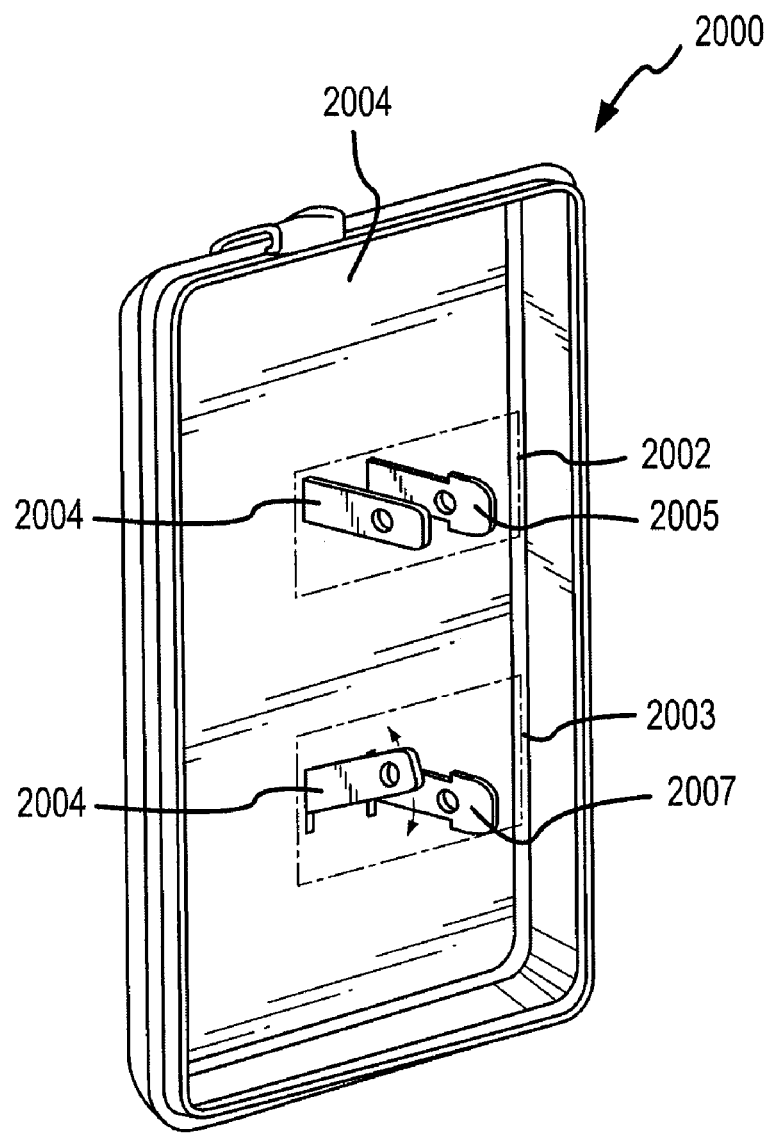
FIG. 20 is a perspective view of an exemplary device having adjustable outlet prongs.

For example, with reference to FIG. 20, an example of a wall-mounted device 20000 (such as an air freshener, battery charger or the like) in accordance with the present invention suitably includes a housing 2001 and two or more outlet plugs 2002 and 2003 capable of electrically interfacing with an electrical receptacle having two or more outlets. For example, the non-limiting embodiment shown in FIG. 2004 is a "duplex" device.

In the context of a duplex embodiment, each of the two plugs 2002 and 2003 suitably include two or more outlet prongs (e.g. prongs 2004 and 2005 for plug 2002, and prongs 2006 and 2007 for plug 2003) that can be inserted into the holes of a conventional electrical receptacle. In accordance with various electrical standards, one of the prongs 2005/2007 corresponding to the electrically active or "hot" portion of the electrical receptacle may be slightly larger in size than the other prong 2006/2001, which generally corresponds to "neutral" or "ground". Although not shown in FIG. 20, a third "ground" prong may also be present on alternate embodiments of each electrical plug 2002/2003.

Because device 20000 includes multiple plugs 2002/2003, each of which is designed to be inserted into one outlet in a multi-outlet receptacle, each prong 2006/2007 of one or more of the plugs 2003 is configured to adapt or otherwise move, rotate, translate, etc. and/or to accommodate receptacles of varying dimensions. For example, in one embodiment, each prong 2006/2007 is free to move within the confines of a slot 2008 formed in housing 2001. The size of slot 2008 suitably corresponds to the extent of movement required by a particular embodiment. For device 2000 to accommodate both conventional North American standard and GFCI duplex receptacles, for example, a movement of about ⅛-¼ inch (or about 1-4 millimeters) may be sufficient. Of course the exact amount of movement needed will vary from embodiment to embodiment, and may be based upon electrical standards, building codes and the like.

In various embodiments, to adapt, as a user inserts device 2000 into an electrical receptacle, the movable prongs 2006/2007 suitably translate and/or rotate as appropriate to interface with the outlet. For example, in the embodiment shown in FIG. 20, prongs 2004/2005 are inserted into the topmost outlet of the receptacle, and movable prongs 2006/2007 suitably adjust to the outlet holes of the bottom outlet as device 20000 is inserted into the receptacle. Prong placement and insertion may be further aided by designing the length of prongs 2006/2007 to be shorter than the length of non-movable prongs 2004/2005, for example, or by shaping movable prongs 2006/2007 with a beveled, slanted, rounded or similar-shaped edge.

Figure 21A:
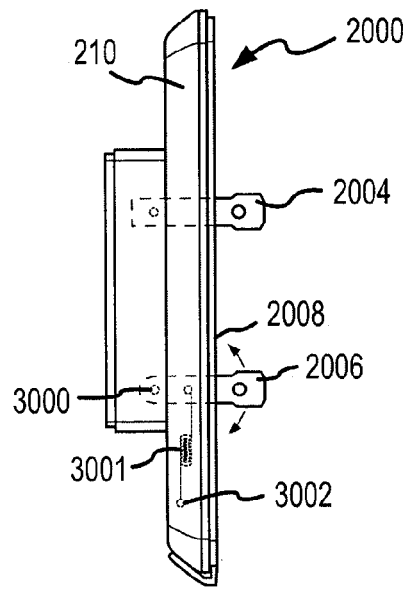
FIG. 21A is a cutaway side view of an exemplary device having a rotatable outlet prong.

With reference now to FIG. 21A, a device 2000 which adapts via rotatable prongs 2006/2007 is shown. Although prong 2007 is not visible in the view shown in FIG. 3A, the structures shown for prong 2006 could be readily implemented on the other prongs of device 2000. Prong 2006 is suitably fashioned with a notch or hole that is capable of accepting a pin 3000 or other outcropping so that the pin serves as a pivot point for prong 2006. Pin 3000 is any pivot point that is rigidly fixed with respect to housing 2001. In one embodiment, pin 3000 is fashioned as an outcropping of housing 2001 through appropriate fabrication techniques such as injection molding. Alternatively, pin 3000 may be implemented as a separate metal, plastic other object that may be inserted into a groove, hole or other recession in housing 2001 such that pin 3000 is rigidly held in place. A spring 3001 or other elastic member (such as a plastic finger, a rubber band, or any other structure) may be optionally provided to bias prong 2006 into a desired initial position or to hold prong 2006 in place prior to or after insertion. Spring 3001 may be coupled to any point of prong 2006, and may be attached to housing 2001 at any anchor point 3002.

In this embodiment, prong 2006 rotates about pin 3000 in response to the position of the outlet receptacle to adapt to the receptacle. For example, as an external force is applied to device 2000, prong 2006 suitably rotates about pin 3000 such that prong 2006 is guided within slot 2008 to the outlet hole as appropriate. As with the prior embodiments, prong 2006 may be shaped in any convenient fashion to assist in guiding prong 2006 to the outlet hole.

Figure 21B:
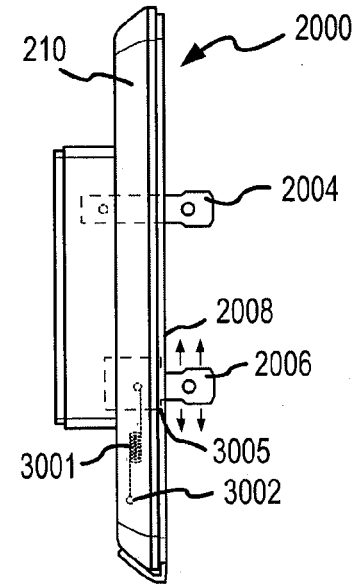
FIG. 21B is a cutaway side view of an exemplary device having a translatable outlet prong.

With reference now to FIG. 21B, another exemplary embodiment of a device 2000 suitably includes one or more prongs 2006/2007 that adapt by translation with respect to housing 2001 to accommodate receptacles of varying dimensions. Prong 2006 suitably has a front face 3005 that interfaces with housing 2001 to allow prong 2006 to slide or otherwise laterally move within the confines of groove 2008. In a further embodiment, prong 2006 includes a tongue, flange or other outcropping that slides within a groove or other guide on housing 2001 to guide the lateral movement of prong 2006 with respect to housing 2001. As with the prior embodiment, an optional spring 3001 or other biasing mechanism may also be provided to bias prong 2006 toward an anchor point 3002 or other point on housing 2001. Similar to the rotational embodiment described above, in operation, an insertion force provided by the user overcomes the bias force of spring 3001 to allow prong 2006 to move laterally within groove 2008 to interface with the outlet receptacle.

Figure 21C:
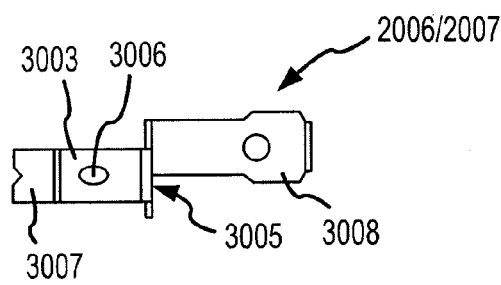
FIGS. 21C-D are side and top views, respectively, of an exemplary outlet prong.
Figure 21D:
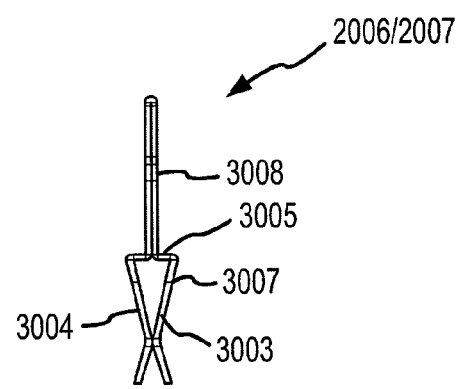

FIGS. 21C-D are side and top views, respectively, of an exemplary prong 2006/2007 that may be used to implement rigid or movable prongs in a device 2000. With reference to FIGS. 21C-D, an exemplary prong 3000 suitably includes two legs 3003 and 3004 that receive the prongs of an external appliance such as a hair dryer, lamp, curling iron, kitchen appliance or the like. Prong 2006/2007 also includes a front face 3005 that slides or rotates with respect to housing 2001 as described above in conjunction with FIGS. 21A-B, and may include a hole 3006 in any appropriate location to receive spring 3001 or another elastic biasing member. As best seen in FIG. 21C, prongs 2006/2007 may be formed such that the portion 3007 internal to housing 2001 (FIG. 20) is not aligned with the external portion 3008. In such embodiments, the non-linear structure of prong 2006/2007 further enhances rotation, translation or other movement as may be appropriate. Prongs 2006/2007 may be fashioned from any available material such as metal or plastic. In a further embodiment, prongs 2006/2007 are made from an electrically-conductive material such as copper, aluminum or the like.

Figure 22A:
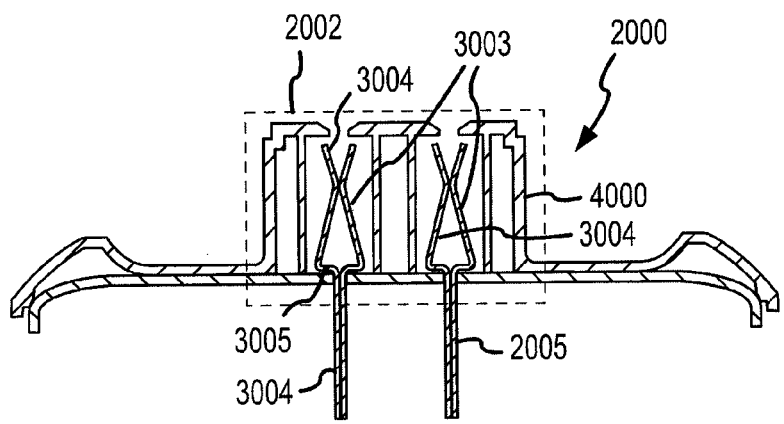
FIGS. 22A-B are cross-sectional views of an exemplary vapor dispensing device.
Figure 22B:
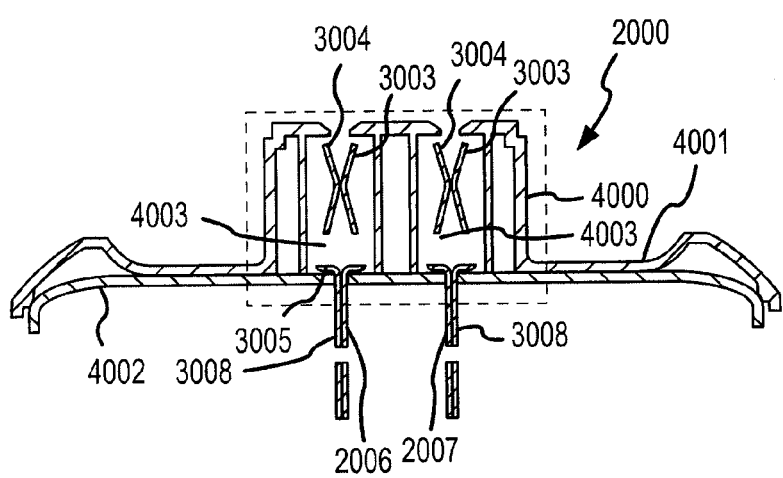

FIGS. 22A-B show top and cutaway views of a device which adapts using movable outlet prongs similar to the device illustrated in FIGS. 21A-D. An exemplary device 2000 suitably includes a housing with one or more outlet faces 4000 capable of receiving the prongs of an electrical plug from an external device (e.g. a radio, hair dryer, curling iron, electric razor, clock, lamp, kitchen appliance, or the like). Outlet faces 4000 suitably correspond to the two electrical plugs 2002/2003 disposed within housing 2001, as described more fully below. Housing 2001 may be fashioned of thermoformed or injection-molded plastic, metal, ceramic, glass or any other convenient material. Either or both of plugs 2002 and 2003 may be formed with the exemplary structures shown in FIGS. 22A-B, or with any other plug structure.

With reference to FIGS. 22A-B, housing 2001 of device 2000 suitably includes a front face 4001 and a back face 4002 encompassing plugs 2002/2003, as well as the various components applicable to the type of device the present invention is embodied in. Each plug 2002/2003 includes a set of prongs 2004/2005, 2006/2007 that interface with the prongs of an external device. In the stationary prong structure shown in FIG. 22A, each prong 2004/2005 is formed to include legs 3005/3003 as described above to electrically connect the prongs of the external device with one of the outlets in the receptacle. Prongs 2004/2005 may be formed such that front face 3005 of each prong is rigidly held in place within the back face 4002 to prevent movement of the prongs with respect to housing 2001. In the movable structure shown in FIG. 22B, the prongs of an external device are guided and held in place by legs 3003 and 3004, which may be physically isolated from the external sliding portion 3008 (FIG. 21C). A gap 4003 may be provided such that prongs 2006/2007 are allowed to translate along front face 3005, as guided by slot 2008 (FIG. 20). Alternatively, a rotational, translational or other structure such as those described above could be used.

For the sake of brevity, conventional electrical and mechanical design techniques used in developing various multiplexing devices (and the various components thereof) are not described in detail herein. Accordingly, devices disclosed herein may be readily modified to create equivalent embodiments through application of general electrical and mechanical principles. In a still further embodiment, the uppermost set of prongs may be configured to adjust to variations in receptacle size in addition to or in place of the lowermost prongs, as shown in the Figures herein. Moreover, although the general concepts of self-adjustability have been described with reference to a vapor dispensing device herein, these concepts may be readily applied to other equivalent electrical devices such as air filters, nightlights, audio speakers, wireless control devices, timers and the like.

Finally, while the present invention has been described above with reference to various exemplary embodiments, many changes, combinations and modifications may be made to the exemplary embodiments without departing from the scope of the present invention. For example, the various components may be implemented in alternate ways. These alternatives can be suitably selected depending upon the particular application or in consideration of any number of factors associated with the operation of the system. In addition, the techniques described herein may be extended or modified for use with other types of devices. These and other changes or modifications are intended to be included within the scope of the present invention.

The invention claimed is:

1. A vapor-dispensing device configured to connect to and mimic an electrical receptacle having a first outlet, said vapor-dispensing device comprising:
   a housing having a first device outlet and a second device outlet, said first device outlet and said second device outlet defining an outlet pattern having at least one lateral support surface and at least one horizontal support surface, said housing configured to be removably attached to the first outlet and having the same profile as the electrical receptacle; and
   a refill configured to removably attach to the vapor-dispensing device, said refill body configured to be received on said at least one lateral support surface and said at least one horizontal support surface of said outlet pattern; and
   a volatizable material provided within said refill.

2. A vapor dispensing device in accordance with claim 1, further comprising an outwardly extending structure and said refill having an aperture configured in substantially the same size as said outwardly extending structure such that said refill can be attached to said housing and said refill has a thickness substantially equal to the distance the outwardly extending structure extends.

3. A vapor dispensing device in accordance with claim 1, wherein said refill is configured as a U-shape.

4. A vapor dispensing device in accordance with claim 1, wherein said refill is configured as an L-shape.

5. A vapor dispensing device in accordance with claim 1, wherein said refill is configured as a C-shape.

6. A vapor dispensing device in accordance with claim 1, wherein said refill has a window for viewing said volatizable material in said refill.

7. A vapor dispensing device in accordance with claim 1, said volatizable material is volatized with a heating element.

8. A vapor dispensing device in accordance with claim 1, said volatizable material is volatized passively.

9. A vapor dispensing device in accordance with claim 1, further comprising a fragrance delivery system having a chamber, an eminator, a first wick and a second wick proximate to said eminator, and wherein said first and second wicks in fluid communication with said refill.

10. A vapor dispensing device in accordance with claim 1, further comprising a fragrance delivery system having a chamber, an eminator, a first wick and a second wick in contact with said eminator, and wherein said first and second wicks in fluid communication with said refill.

11. A vapor dispensing device in accordance with claim 9, wherein said eminator has a surface area of about 9 cm, and said first and second wicks have lengths of about 10 cm and widths of about 0.5 cm.

12. A vapor dispensing device in accordance with claim 9, wherein said first and second wicks are separated from said eminator by a rip-cord.

* * * * *